(12) United States Patent
Harada et al.

(10) Patent No.: US 9,089,306 B2
(45) Date of Patent: Jul. 28, 2015

(54) BLOOD VESSEL ULTRASONIC IMAGE MEASURING METHOD

(75) Inventors: Chikao Harada, Nagoya (JP); Hiroshi Masuda, Nagoya (JP); Hidenori Suzuki, Nagoya (JP)

(73) Assignee: UNEX CORPORATION, Nagoya-Shi (JP)

( * ) Notice: Subject to any disclaimer, the term of this patent is extended or adjusted under 35 U.S.C. 154(b) by 465 days.

(21) Appl. No.: 12/734,045

(22) PCT Filed: Sep. 16, 2008

(86) PCT No.: PCT/JP2008/066682
§ 371 (c)(1),
(2), (4) Date: Apr. 7, 2010

(87) PCT Pub. No.: WO2009/047966
PCT Pub. Date: Apr. 16, 2009

(65) Prior Publication Data
US 2010/0210946 A1    Aug. 19, 2010

(30) Foreign Application Priority Data

Oct. 9, 2007  (JP) ................. 2007-263805

(51) Int. Cl.
*A61B 5/00* (2006.01)
*A61B 8/00* (2006.01)
(Continued)

(52) U.S. Cl.
CPC .............. *A61B 5/489* (2013.01); *A61B 5/6835* (2013.01); *A61B 8/0891* (2013.01);
(Continued)

(58) Field of Classification Search
USPC .......................... 600/437, 441, 454, 455, 459
See application file for complete search history.

(56) References Cited

U.S. PATENT DOCUMENTS

| 5,329,929 A | * | 7/1994 | Sato et al. ..................... 600/441 |
| 5,891,039 A | | 4/1999 | Bonnefous et al. |

(Continued)

FOREIGN PATENT DOCUMENTS

| EP | 1 550 403 A1 | 7/2005 |
| JP | A-5-89244 | 4/1993 |

(Continued)

OTHER PUBLICATIONS

Oct. 21, 2008 International Search Report issued in corresponding Interrational Application No. PCT/JP2008/066682 (with translation).

(Continued)

*Primary Examiner* — Rochelle Turchen
(74) *Attorney, Agent, or Firm* — Oliff PLC

(57) ABSTRACT

A blood vessel ultrasonic image measuring method capable of facilitating the positioning of an ultrasonic probe and acquiring sufficient positioning accuracy. Because of inclusion of an around-X-axis positioning step of causing a multiaxis driving device to position an ultrasonic probe such that distances from respective ultrasonic array probes to the center of a blood vessel are equalized, and an X-axis direction positioning step and an around-Z-axis positioning step of causing the multiaxis driving device to position the ultrasonic probe such that the image of the blood vessel is positioned at the center portion in the width direction of the first short axis image display area and the second short axis image display area, the positioning may be performed by using the positions in the longitudinal direction of the ultrasonic array probes relative to the blood vessel or the distances of the ultrasonic array probes to the blood vessel.

10 Claims, 24 Drawing Sheets

(51) Int. Cl.
  *G01S 7/52* (2006.01)
  *A61B 8/08* (2006.01)
  *G01S 15/89* (2006.01)

(52) U.S. Cl.
  CPC ............ *A61B 8/4218* (2013.01); *A61B 8/4281* (2013.01); *A61B 8/4483* (2013.01); *A61B 8/4494* (2013.01); *A61B 8/464* (2013.01); *A61B 8/488* (2013.01); *G01S 7/52065* (2013.01); *G01S 15/8936* (2013.01); *G01S 15/8925* (2013.01)

(56) References Cited

U.S. PATENT DOCUMENTS

| | | | |
|---|---|---|---|
| 6,328,693 | B1 | 12/2001 | Miyatake et al. |
| 6,503,201 | B1 | 1/2003 | Liu et al. |
| 2007/0055152 | A1 | 3/2007 | Ukubo et al. |

FOREIGN PATENT DOCUMENTS

| | | |
|---|---|---|
| JP | A-10-192278 | 7/1998 |
| JP | A-2000-217815 | 8/2000 |
| JP | A-2001-104312 | 4/2001 |
| JP | A-2001-157677 | 6/2001 |
| JP | A-2003-126089 | 5/2003 |
| JP | A-2003-245280 | 9/2003 |
| JP | A-2005-328948 | 12/2005 |
| JP | A-2006-6686 | 1/2006 |
| JP | A-2007-90049 | 4/2007 |
| JP | A-2007-229517 | 9/2007 |

OTHER PUBLICATIONS

Chinese Office Action issued in Application No. 200880111011.X; Dated Jun. 23, 2011 (With Translation).
Extended European Search Report in Application No. 08837581.1 mailed Nov. 27, 2013.
Oct. 2, 2014 Notification for Filing an Argument issued in Korean Patent Application No. 10-2010-7007968.
Nov. 25, 2014 Communication pursuant to Article 94(3) EPC issued in European Patent Application No. 08 837 581.1-1660.
Apr. 30, 2015 Korean Office Action issued in Korean Patent Application No. 10-2010-7007968.

* cited by examiner a=b
c=d a=b
c=d
e>f a=b
c=d
e=f

BLOOD VESSEL ULTRASONIC IMAGE MEASURING METHOD

TECHNICAL FIELD

The present invention relates to a blood vessel ultrasonic image measuring method, which accurately positions an ultrasonic probe on a blood vessel of a living body.

BACKGROUND ART

An ultrasonic array probe having a plurality of ultrasonic transmitters linearly arranged is used for measuring a diameter of a blood vessel under skin of a living body. For example, Patent Document 1 proposes an apparatus that uses and H-shaped ultrasonic probe made up of a first and second ultrasonic array probes in parallel with each other and a third ultrasonic array probe linking the intermediate potions thereof to measure a blood flow velocity, arterial vessel wall thickness and lumen diameter, etc., by positioning the third ultrasonic array probe in parallel with an arterial vessel. However, since the ultrasonic probe is positioned by manual operation of an operator, a lot of skill is required and, if a subject moves, it is problematically difficult to follow the movement.

DISCLOSURE OF THE INVENTION

Problems to be Solved by the Invention

In contrast, as described in Patent Document 2, a positioning method is employed that uses the steps of positioning the barycenter of a color Doppler signal at the center of a blood vessel; moving an ultrasonic array probe in the longitudinal direction such that the blood vessel center conforms to the image center; and subsequently rotating the ultrasonic array probe around the center of the longitudinal direction to be parallel with the blood vessel and then translating and positioning the ultrasonic array probe on the center of the blood vessel. However, in this method, especially, at the step of translating and positioning the ultrasonic array probe in parallel with the blood vessel on the center of the blood vessel, the positioning of the ultrasonic probe requires troublesome and time consuming signal process and control and the positioning accuracy is not obtained.

Patent Document 1: Japanese Patent Application Laid-Open Publication No. 10-192278

Patent Document 2: Japanese Patent Application Laid-Open Publication No. 2003-245280

The present invention was conceived in view of the situations and it is therefore the object of the present invention to provide a blood vessel ultrasonic image measuring method capable of facilitating the positioning of an ultrasonic probe and acquiring sufficient positioning accuracy.

Means for Solving the Problems

The object indicated above is achieved in the first mode of the present invention, which provides a blood vessel ultrasonic image measuring method using (a) an ultrasonic probe including a first short axis ultrasonic array probe and a second short axis ultrasonic array probe parallel to each other on one flat surface, the first short axis ultrasonic array probe and the second short axis ultrasonic array probe having a plurality of ultrasonic transducers linearly arranged along a direction parallel to an X-axis direction, (b) a positioning device capable of being rotated around the X-axis, moved in the X-axis direction, and rotated around a Z-axis that passes through a longitudinal center portion of the first short axis ultrasonic array probe and that is orthogonal to the one flat surface, and (c) an image displaying device including a first short axis image display area that displays an ultrasonic image from the first short axis ultrasonic array probe and a second short axis image display area that displays an ultrasonic image from the second short axis ultrasonic array probe to bring the ultrasonic probe into contact with skin of a living body for measuring an ultrasonic image of a blood vessel under the skin of the living body, the method comprising; (d) an around-X-axis positioning step of causing the positioning device to position the ultrasonic probe around the X-axis such that distance from the first short axis ultrasonic array probe to center of the blood vessel becomes equal to distance from the second short axis ultrasonic array probe to the center of the blood vessel; (e) an X-axis direction positioning step of causing the positioning device to translate the ultrasonic probe in the X-axis direction such that an image of the blood vessel is positioned at a center portion in width direction of the first short axis image display area; and (f) an around-Z-axis positioning step of causing the positioning device to rotate the ultrasonic probe around the Z-axis such that an image of the blood vessel is positioned at a center portion in width direction of the second short axis image display area.

The object indicated above is achieved in the second mode of the present invention, which provides the blood vessel ultrasonic image measuring method of the first mode of the invention, wherein (g) the X-axis is an axis passing under the skin, wherein (h) at the around-X-axis positioning step, the ultrasonic probe is positioned around the X-axis.

The object indicated above is achieved in the third mode of the present invention, which provides the blood vessel ultrasonic image measuring method of the first or second mode of the invention, wherein (i) the ultrasonic probe further includes a long axis ultrasonic array probe abutting on the first short axis ultrasonic array probe and/or the second short axis ultrasonic array probe and having a plurality of ultrasonic transducers linearly arranged in a Y-axis direction orthogonal to the X-axis direction, wherein (j) the Z-axis passes through an intersecting point between longitudinal direction of the first short axis ultrasonic array probe and longitudinal direction of the long axis ultrasonic array probe and is orthogonal to the X-axis direction and the Y-axis direction, wherein (k) the image displaying device includes a long axis image display area that abuts on the first short axis image display area and/or the second short axis image display area and that displays an ultrasonic image from the long axis ultrasonic array probe, and wherein the first short axis image display area, the second short axis image display area, and the long axis image display area has a common longitudinal axis indicative of a depth dimension from the skin.

The object indicated above is achieved in the fourth mode of the present invention, which provides the blood vessel ultrasonic image measuring method of the third mode of the invention, comprising (1) a blood vessel diameter calculating step of calculating lumen diameter of the blood vessel based on a long axis image signal of the blood vessel detected by the long axis ultrasonic array probe.

The object indicated above is achieved in the fifth mode of the present invention, which provides the blood vessel ultrasonic image measuring method of the third or fourth mode of the invention, comprising (m) a blood vessel membrane thickness calculating step of calculating intima thickness and/or intima-media thickness of the blood vessel based on the long axis image signal of the blood vessel detected by the long axis ultrasonic array probe.

The object indicated above is achieved in the sixth mode of the present invention, which provides the blood vessel ultrasonic image measuring method of any one of the first to fifth modes of the invention, (n) wherein the first short axis ultrasonic array probe and the second short axis ultrasonic array probe emits ultrasonic obliquely in direction at predetermined angles to the blood vessel toward upstream or downstream of the blood vessel.

The object indicated above is achieved in the seventh mode of the present invention, which provides the blood vessel ultrasonic image measuring method of the sixth mode of the invention, comprising (o) an image correcting step of correcting short axis ultrasonic images respectively displayed in the first short axis image display area and the second short axis image display area based on the predetermined angles to form images in a state that the ultrasonic emission direction of the first short axis ultrasonic array probe and the second short axis ultrasonic array probe is orthogonal to the blood vessel when short axis ultrasonic images of the blood vessel respectively detected by the first short axis ultrasonic array probe and the second short axis ultrasonic array probe are respectively displayed in the first short axis image display area and the second short axis image display area.

The object indicated above is achieved in the eighth mode of the present invention, which provides the blood vessel ultrasonic image measuring method of any one of the first to seventh modes of the invention, (p) wherein at the around-X-axis positioning step, the X-axis direction positioning step, or the around-Z-axis positioning step, pattern recognition is executed for recognizing an image of the blood vessel.

The object indicated above is achieved in the ninth mode of the present invention, which provides the blood vessel ultrasonic image measuring method of the eighth mode of the invention, (q) wherein the pattern recognition is executed with a Doppler signal included in the image of the blood vessel in the ultrasound images in the first short axis image display area and the second short axis image display area from the first short axis ultrasonic array probe and the second short axis ultrasonic array probe.

The object indicated above is achieved in the tenth mode of the present invention, which provides the blood vessel ultrasonic image measuring method of any one of the first to ninth modes of the invention, comprising (r) a blood vessel parameter calculating step of calculating the lumen diameter and/or the intima-media thickness of the blood vessel based on a short axis image signal of the blood vessel detected by the first short axis ultrasonic array probe or the second short axis ultrasonic array probe.

The object indicated above is achieved in the eleventh mode of the present invention, which provides the blood vessel ultrasonic image measuring method of the third mode of the invention, comprising (s) a step of displaying a symbol in a positioning state display area, the symbol in the positioning state display area moving along one of a first direction and a second direction orthogonal to each other to indicate distances from a short axis image of the blood vessel displayed in the first short axis image display area to edges on both sides of the first short axis image display area, the symbol moving along the other of the first direction and the second direction orthogonal to each other to indicate distances from a short axis image of the blood vessel displayed in the second short axis image display area to edges on both sides of the second short axis image display area, the symbol tilting to indicate a difference between a distance from the short axis image of the blood vessel displayed in the first short axis image display area to the upper edge or the lower edge of the first short axis image display area and a distance from the short axis image of the blood vessel displayed in the second short axis image display area to the upper edge or the lower edge of the second short axis image display area.

The object indicated above is achieved in the twelfth mode of the present invention, which provides the blood vessel ultrasonic image measuring method of the third mode of the invention, comprising (t) a step of storing an image of the blood vessel displayed in the long axis image display area as a first image and registering a portion in longitudinal direction of the image of the blood vessel as a first template in advance, (u) a step of storing an image of the blood vessel displayed in the long axis image display area as a second image when a portion in the longitudinal direction of the image of the blood vessel identical to the first template arrives at an end of the long axis image display area set in advance in the course of movement of the ultrasonic probe along the blood vessel and registering the portion in the longitudinal direction of the image of the blood vessel as a second template, (v) a step of storing an image of the blood vessel displayed in the long axis image display area as a third image when a portion in the longitudinal direction of the image of the blood vessel identical to the second template arrives at an end of the long axis image display area set in advance in the course of further movement of the ultrasonic probe along the blood vessel, and (w) a step of synthesizing and displaying in a synthetic long axis image display area one long axis image longer than longitudinal dimension of the image of the blood vessel from the first image, the second image, and the third image.

Effects of the Invention

According to the blood vessel ultrasonic image measuring method of the first mode of the invention, the method includes (d) an around-X-axis positioning step of causing the positioning device to position the ultrasonic probe around the X-axis such that distance from the first short axis ultrasonic array probe to center of the blood vessel becomes equal to distance from the second short axis ultrasonic array probe to the center of the blood vessel; (e) an X-axis direction positioning step of causing the positioning device to translate the ultrasonic probe in the X-axis direction such that an image of the blood vessel is positioned at a center portion in width direction of the first short axis image display area; and (f) an around-Z-axis positioning step of causing the positioning device to rotate the ultrasonic probe around the Z-axis such that an image of the blood vessel is positioned at a center portion in width direction of the second short axis image display area. Consequently, the positioning may be performed by using the positions in the longitudinal direction of the ultrasonic array probes relative to the blood vessel or the distances of the ultrasonic array probes to the blood vessel and, therefore, the ultrasonic probe may simply and easily be positioned on the blood vessel of the living body with higher accuracy.

According to the blood vessel ultrasonic image measuring method of the second mode of the invention, (g) the X-axis is an axis passing under the skin, wherein (h) at the around-X-axis positioning step, the ultrasonic probe is positioned around the X-axis. Consequently, the condition of pressing the skin by the first short axis ultrasonic array probe and the second short axis ultrasonic array probe may not significantly be changed to change the distances between the probes and the blood vessel. Preferably, the X-axis is located immediately under the first short axis ultrasonic array probe. In this case, almost no change is made in the condition of pressing the skin by the first short axis ultrasonic array probe and the distance between the first short axis ultrasonic array probe and the blood vessel.

According to the blood vessel ultrasonic image measuring method of the third mode of the invention, (i) the ultrasonic probe further includes a long axis ultrasonic array probe abutting on the first short axis ultrasonic array probe and/or the second short axis ultrasonic array probe and having a plurality of ultrasonic transducers linearly arranged in a Y-axis direction orthogonal to the X-axis direction, wherein (j) the Z-axis passes through an intersecting point between longitudinal direction of the first short axis ultrasonic array probe and longitudinal direction of the long axis ultrasonic array probe and is orthogonal to the X-axis direction and the Y-axis direction, wherein (k) the image displaying device includes a long axis image display area that abuts on the first short axis image display area and/or the second short axis image display area and that displays an ultrasonic image from the long axis ultrasonic array probe, and wherein the first short axis image display area, the second short axis image display area, and the long axis image display area has a common longitudinal axis indicative of a depth dimension from the skin. Consequently, the long axis ultrasonic array probe is preferably positioned on the center of the blood vessel.

According to the blood vessel ultrasonic image measuring method of the fourth mode of the invention, the method includes (l) a blood vessel diameter calculating step of calculating lumen diameter of the blood vessel based on a long axis image signal of the blood vessel detected by the long axis ultrasonic array probe. Consequently, the blood vessel diameter may accurately be acquired.

According to the blood vessel ultrasonic image measuring method of the fifth mode of the invention, the method includes (m) a blood vessel membrane thickness calculating step of calculating intima thickness and/or intima-media thickness of the blood vessel based on the long axis image signal of the blood vessel detected by the long axis ultrasonic array probe. Consequently, the intima thickness and the intima-media thickness of the blood vessel may accurately be acquired.

According to the blood vessel ultrasonic image measuring method of the sixth mode of the invention, (n) the first short axis ultrasonic array probe and the second short axis ultrasonic array probe emits ultrasonic obliquely in direction at predetermined angles to the blood vessel toward upstream or downstream of the blood vessel. Consequently, the blood flow velocity becomes measurable with the ultrasound Doppler.

According to the blood vessel ultrasonic image measuring method of the seventh mode of the invention, the method includes (o) an image correcting step of correcting short axis ultrasonic images respectively displayed in the first short axis image display area and the second short axis image display area based on the predetermined angles to form images in a state that the ultrasonic emission direction of the first short axis ultrasonic array probe and the second short axis ultrasonic array probe is orthogonal to the blood vessel when short axis ultrasonic images of the blood vessel respectively detected by the first short axis ultrasonic array probe and the second short axis ultrasonic array probe are respectively displayed in the first short axis image display area and the second short axis image display area. Consequently, the blood flow velocity becomes measurable with the ultrasound Doppler and the short axis ultrasonic images respectively displayed in the first short axis image display area and the second short axis image display area are formed as accurate cross-section images.

According to the blood vessel ultrasonic image measuring method of the eighth mode of the invention, (p) at the around-X-axis positioning step, the X-axis direction positioning step, or the around-Z-axis positioning step, pattern recognition is executed for recognizing an image of the blood vessel. Consequently, the ultrasonic probe may simply and easily be positioned on the blood vessel of the living body with higher accuracy.

According to the blood vessel ultrasonic image measuring method of the ninth mode of the invention, (q) the pattern recognition is executed with a Doppler signal included in the image of the blood vessel in the ultrasound images in the first short axis image display area and the second short axis image display area from the first short axis ultrasonic array probe and the second short axis ultrasonic array probe. Consequently, more accurate pattern recognition is enabled.

According to the blood vessel ultrasonic image measuring method of the tenth mode of the invention, the method includes (r) a blood vessel parameter calculating step of calculating the lumen diameter and/or the intima-media thickness of the blood vessel based on a short axis image signal of the blood vessel detected by the first short axis ultrasonic array probe or the second short axis ultrasonic array probe. Consequently, the lumen diameter and the intima-media thickness may accurately be acquired.

According to the blood vessel ultrasonic image measuring method of the eleventh mode of the invention, the method includes (s) a step of displaying a symbol in a positioning state display area, the symbol in the positioning state display area moving along one of a first direction and a second direction orthogonal to each other to indicate distances from a short axis image of the blood vessel displayed in the first short axis image display area to edges on both sides of the first short axis image display area, the symbol moving along the other of the first direction and the second direction orthogonal to each other to indicate distances from a short axis image of the blood vessel displayed in the second short axis image display area to edges on both sides of the second short axis image display area, the symbol tilting to indicate a difference between a distance from the short axis image of the blood vessel displayed in the first short axis image display area to the upper edge or the lower edge of the first short axis image display area and a distance from the short axis image of the blood vessel displayed in the second short axis image display area to the upper edge or the lower edge of the second short axis image display area. Consequently, the right and the wrong of the positioning of the ultrasonic probe may visually and instantly be checked based on the position and the tilt of the symbol.

According to the blood vessel ultrasonic image measuring method of the twelfth mode of the invention, the method includes (t) a step of storing an image of the blood vessel displayed in the long axis image display area as a first image and registering a portion in longitudinal direction of the image of the blood vessel as a first template in advance, (u) a step of storing an image of the blood vessel displayed in the long axis image display area as a second image when a portion in the longitudinal direction of the image of the blood vessel identical to the first template arrives at an end of the long axis image display area set in advance in the course of movement of the ultrasonic probe along the blood vessel and registering the portion in the longitudinal direction of the image of the blood vessel as a second template, (v) a step of storing an image of the blood vessel displayed in the long axis image display area as a third image when a portion in the longitudinal direction of the image of the blood vessel identical to the second template arrives at an end of the long axis image display area set in advance in the course of further movement of the ultrasonic probe along the blood vessel, and (w) a step of synthesizing and displaying in a synthetic long axis image display area one long axis image longer than longitudinal dimension of the image of the blood vessel from the first image, the second image, and the third image. Consequently, the long axis image of the blood vessel longer than the length of the long axis ultrasonic array probe C may be acquired.

EXPLANATIONS OF LETTERS OR NUMERALS

14: living body
18: skin
20: blood vessel
24, 102, 112: ultrasonic probe
26: multiaxis driving device (positioning device)
27: probing surface (flat surface)
30: monitor screen displaying device (image displaying device)
104: symbol
$a_1$ to $a_n$: ultrasonic transducer (ultrasonic oscillator)
A: first short axis ultrasonic array probe
B: second short axis ultrasonic array probe
C: long axis ultrasonic array probe
G1: first short axis image display area
G2: second short axis image display area
G3: long axis image display area
G4: positioning state display area
G5: long axis synthetic image display area
S2 to S15: around-X-axis positioning step
S2 to S12, S16 to S19: X-axis direction positioning step
S2 to S12, S16, S20 to S23: around-Z-axis positioning step
S25: blood vessel diameter calculating step, blood vessel membrane thickness calculating step

BEST MODES FOR CARRYING OUT THE INVENTION

Embodiments of the present invention will now be described with reference to the drawings. In the following embodiments, simplification or modification is made as needed and dimension ratios, shapes, etc., of respective portions are not necessarily precisely depicted in the figures.

First Embodiment

Figure 1:
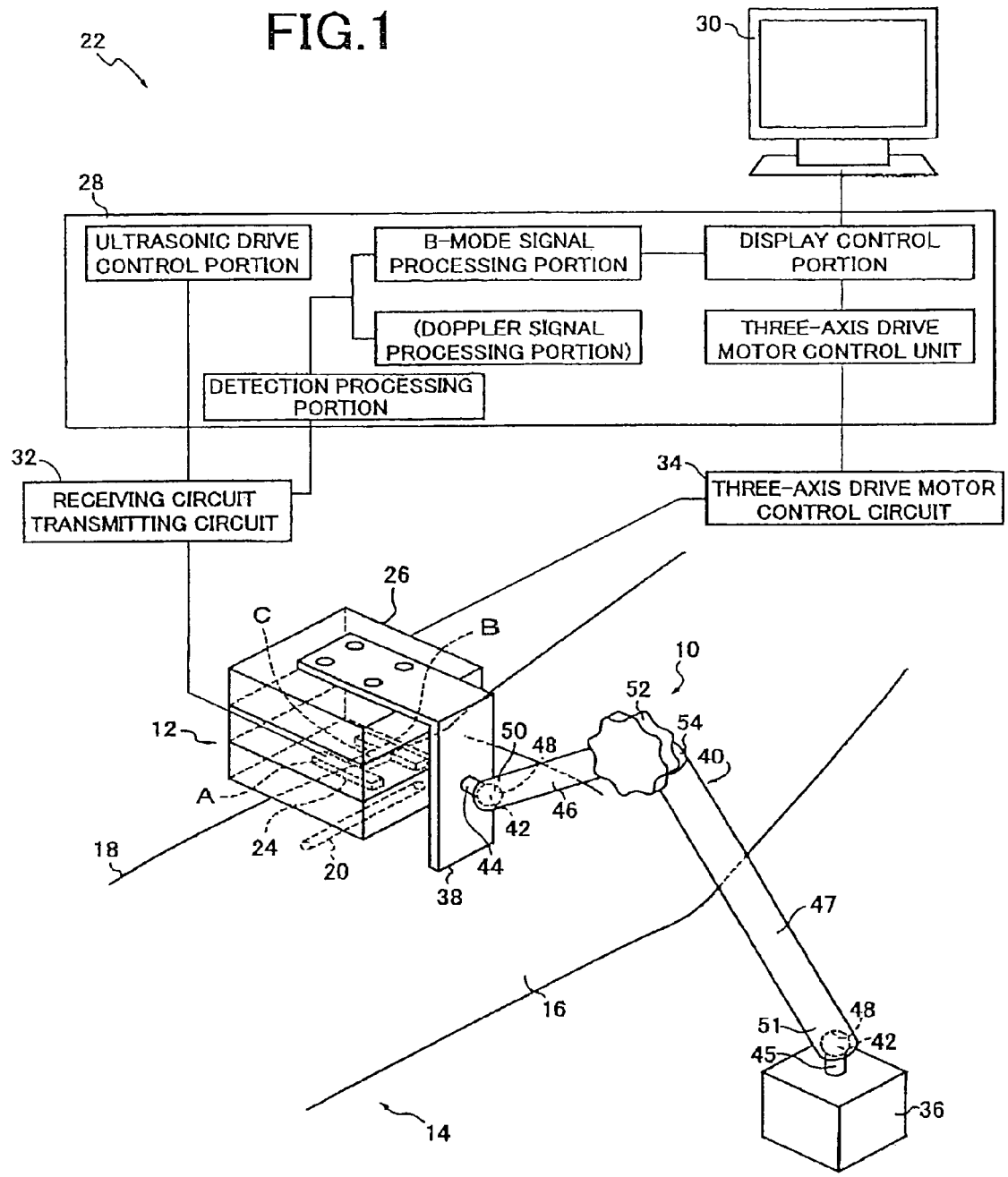
FIG. 1 is a diagram for explaining an overall configuration of a blood vessel ultrasonic image measuring apparatus using a blood vessel ultrasonic image measuring method, which is an embodiment of the present invention.

FIG. 1 is a diagram for explaining an overall configuration of a blood vessel ultrasonic image measuring apparatus 22 using a hybrid probe unit 12 held by a sensor holder 10 to measure a cross-section image (short axis image) or a longitudinal-section image (long axis image) of a blood vessel 20 located immediately below skin 18 from the top face of the skin 18 of an upper arm 16 of a living body 14.

The hybrid probe unit 12 acts as a sensor for detecting biological information related to the blood vessel, i.e., a blood vessel parameter and includes an H-shaped ultrasonic probe 24 made up of two lines of a first short axis ultrasonic array probe A and a second short axis ultrasonic array probe B parallel to each other and a long axis ultrasonic array probe C linking the longitudinal center potions thereof on one flat surface, i.e., a flat probing surface 27, and a multiaxis driving device (positioning device) 26 for positioning the ultrasonic probe 24. The first short axis ultrasonic array probe A, the second short axis ultrasonic array probe B, and the long axis ultrasonic array probe C are respectively formed in longitudinal shapes by linearly arranging a plurality of ultrasonic transducers (ultrasonic oscillators) $a_1$ to $a_n$ made of piezoelectric ceramic, for example.

Figure 2:
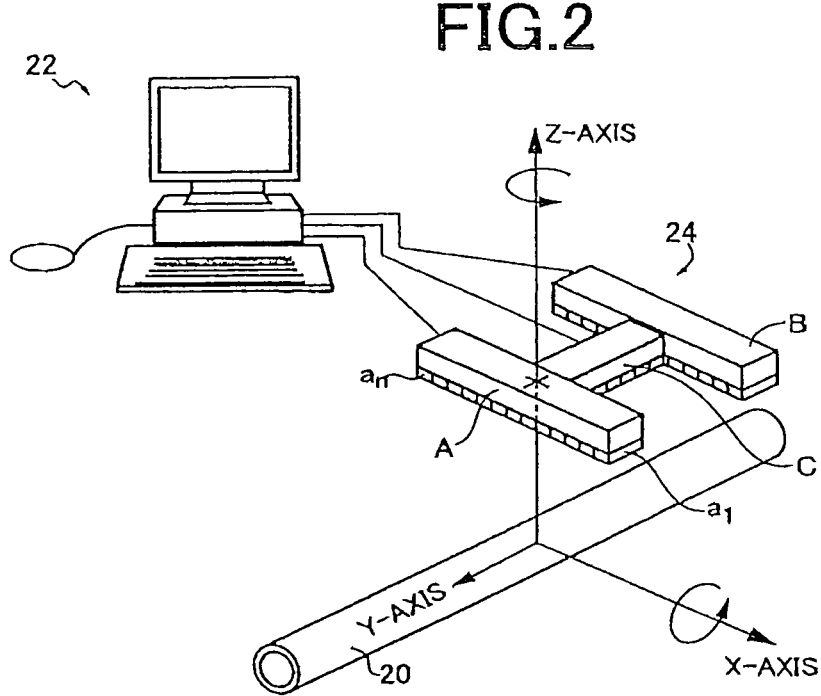
FIG. 2 is a diagram for explaining XYZ-axis orthogonal coordinate axes for representing a posture of an ultrasonic probe of FIG. 1 relative to a blood vessel.

FIG. 2 is for the purpose of explaining XYZ-axis orthogonal coordinate axes used in this embodiment; the X-axis is defined as a direction that is parallel to the longitudinal direction of the first short axis ultrasonic array probe A, that is located immediately under the first short axis ultrasonic array probe A, and that passes through or in the vicinity of the blood vessel 20; the Y-axis is defined as a direction that is parallel to the longitudinal direction of the long axis ultrasonic array probe C and that is orthogonal to the X-axis; and the Z-axis is defined as a direction that passes through the intersecting point between the longitudinal direction of the first short axis ultrasonic array probe A and the longitudinal direction of the long axis ultrasonic array probe C and that is orthogonal to the X-axis direction and the Y-axis direction. As described later, the ultrasonic probe 24 is translated in the X-axis direction and rotated around the X-axis and the Z-axis by the multiaxis driving device 26.

Figure 3:
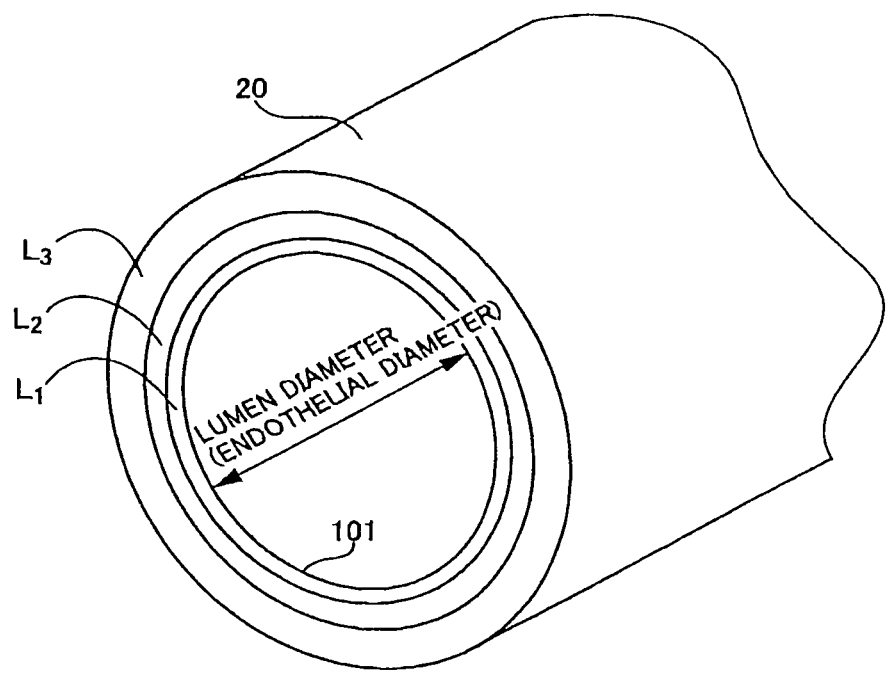
FIG. 3 is an enlarged diagram for explaining a multilayer membrane configuration of a blood vessel displayed on a blood vessel image.

As depicted in FIG. 3, the blood vessel 20 is a brachial artery and has a three-layer configuration consisting of an intima $L_1$, a media $L_2$, and an adventitia $L_3$. An image using ultrasonic displays the intima $L_1$ and the adventitia $L_3$ because the reflection from the media $L_2$ is extremely weak. In an actual image, the inside of the blood vessel 20 and the media $L_2$ are displayed in block while the intima $L_1$ and the adventitia $L_3$ are displayed in white and tissue is displayed as black and white patches. Although the intima $L_1$ is displayed with a thickness significantly thinner than the adventitia $L_3$ and is relatively difficult to be displayed in an image, it is desired to use a rate of change in the diameter of the intima at the time of evaluation of FMD (flow-mediated dilation).

Referring to FIG. 1 again, the blood vessel ultrasonic image measuring apparatus 22 includes an electronic control device 28 made up of a so-called microcomputer, a monitor screen displaying device (image displaying device) 30, an ultrasonic drive control circuit 32, and a three-axis drive motor control circuit 34. The electronic control device 28 supplies a drive signal from the ultrasonic drive control circuit 32 to emit ultrasonic from the first short axis ultrasonic array probe A, the second short axis ultrasonic array probe B, and the long axis ultrasonic array probe C of the ultrasonic probe 24 of the hybrid probe unit 12 and, in response to an ultrasonic reflection signal detected by the first short axis ultrasonic array probe A, the second short axis ultrasonic array probe B, and the long axis ultrasonic array probe C, the ultrasonic reflection signal is processed to generate and display an ultrasonic image under the skin 18 on the monitor screen displaying device 30.

The monitor screen displaying device 30 has a first short axis image display area G1 that displays an ultrasonic image from the first short axis ultrasonic array probe A, a second short axis image display area G2 that displays an ultrasonic image from the second short axis ultrasonic array probe B, and a long axis image display area G3 that displays an ultrasonic image from the long axis ultrasonic array probe C. The first short axis image display area G1, the second short axis image display area G2, and the long axis image display area G3 includes a common longitudinal axis indicative of a depth dimension from the skin 18. When the ultrasonic image of the blood vessel 20 is generated as above, the ultrasonic probe 24 is driven and positioned at a predetermined position relative to the blood vessel 20 by the multiaxis driving device 26 supplied with the drive signal from the three-axis drive motor control circuit 34 by the electronic control device 28. The predetermined position is a position with the first short axis ultrasonic array probe A and the second short axis ultrasonic array probe B made orthogonal to the blood vessel 20 and the long axis ultrasonic array probe C made parallel to the blood vessel 20.

The sensor holder 10 holds the hybrid probe unit 12 in a desired posture at a desired position, i.e., a predetermined position in a three-dimensional space in slight contact with the upper surface of the skin 18 of the upper arm 16 of the living body 14 to the extent that the blood vessel 20 is not deformed. Between the end surface of the ultrasonic probe 24 of the hybrid probe unit 12 and the skin 18, a coupling agent such as jelly is generally interposed that is well known for constraining the attenuation of ultrasonic and the reflection and dispersion at the boundary surface to clarify an ultrasonic image. The jelly is gelatinous water-absorbing polymer containing a high rate of water, for example, agar and has the intrinsic impedance (=sound velocity×density) sufficiently higher than air to significantly constrain the attenuation of ultrasonic transmission/reception signals. A water bag, i.e., a resin bag containing water, olive oil, glycerin, etc., may be used instead of the jelly.

The sensor holder 10 includes a magnetic block 36 fixed to a desk, a pedestal, etc., by the magnetic attracting force, for example; a unit fixing tool 38 to which the hybrid probe unit 12 is fixed, coupling members 44, 45 fixed at one ends to the magnetic block 36 and the unit fixing tool 38 and having tip portions 42 formed into a spherical shape; and a universal arm 40 coupling and supporting the magnetic block 36 and the unit fixing tool 38 via the coupling members 44, 45 in a relatively movable manner. The universal arm 40 has two links 46, 47 rotatably coupled to each other; rotating/bending joint portions 50, 51 respectively including fitting holes 48 fitted with the tip portions 42 in a rotatable and bendable manner with a predetermined resistance applied to the tip portions 42 at one ends of the links 46, 47; and a rotating joint portion 54 at the other ends of the links 46, 47, which links the other ends in a relatively rotatable manner with each other and makes the relative rotation impossible with the clamping force acquired by fastening a threaded fixing knob 52 threaded into a threaded hole provided through the coupling part.

Figure 4A:
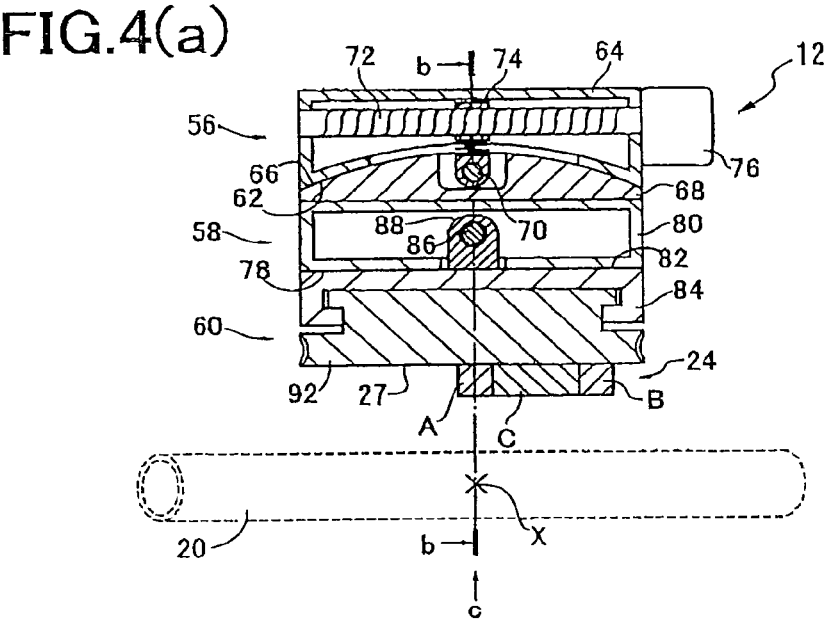
FIG. 4 is a diagram for explaining an X-axis rotating mechanism, an X-axis translating mechanism, and a Z-axis rotating mechanism making up a multiaxis driving device (positioning device) for positioning the ultrasonic probe in a hybrid probe unit of FIG. 1.
Figure 4B:
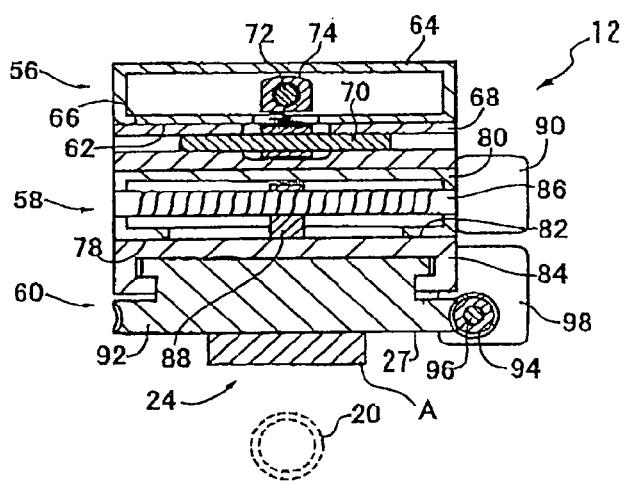
Figure 4C:
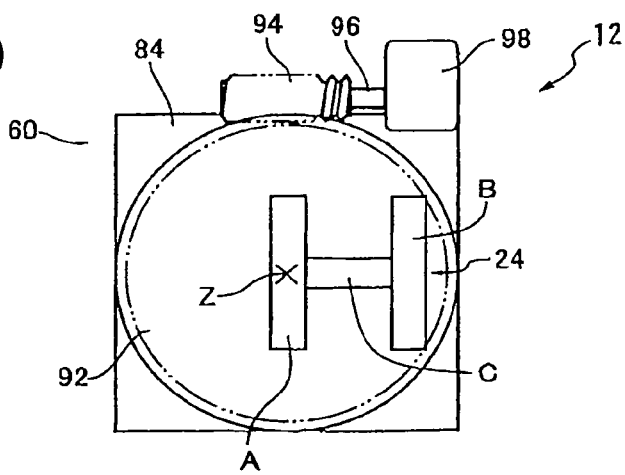

As depicted in FIGS. 4 to 7, the multiaxis driving device 26 is made up of an X-axis rotating (yawing) mechanism 56 for positioning the rotational position of the ultrasonic probe 24 around the X-axis; an X-axis translating mechanism 58 for positioning the translational position of the ultrasonic probe 24 in the X-axis direction; and a Z-axis rotating mechanism 60 for positioning the rotational position of the ultrasonic probe 24 around the Z-axis. FIG. 4 is a diagram for explaining the X-axis rotating mechanism 56, the X-axis translating mechanism 58, and the Z-axis rotating mechanism 60; FIG. 4(a) depicts a longitudinal-section view of the multiaxis driving device 26; FIG. 4(b) depicts a cross-section view taken along line b-b of FIG. 4(a); and FIG. 4(c) depicts a view from an arrow C of FIG. 4(a), The X-axis rotating mechanism 56 acts as an X-axis supporting device that rotatably supports the ultrasonic probe 24 around the X-axis; the X-axis translating mechanism 58 acts as an X-axis supporting device that translatably supports the ultrasonic probe 24 in the X-axis direction; and the Z-axis rotating mechanism 60 acts as an Z-axis supporting device that rotatably supports the ultrasonic probe 24 around the Z-axis.

Figure 5:
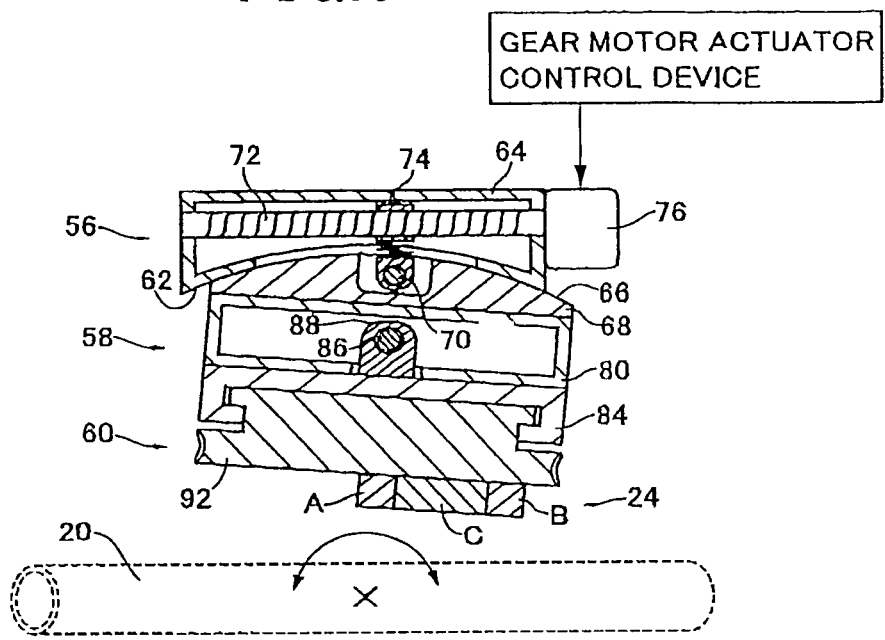
FIG. 5 is a diagram for explaining a state of the ultrasonic probe at the rotational position around the X-axis changed by the X-axis rotating mechanism of FIG. 4.
Figure 6:
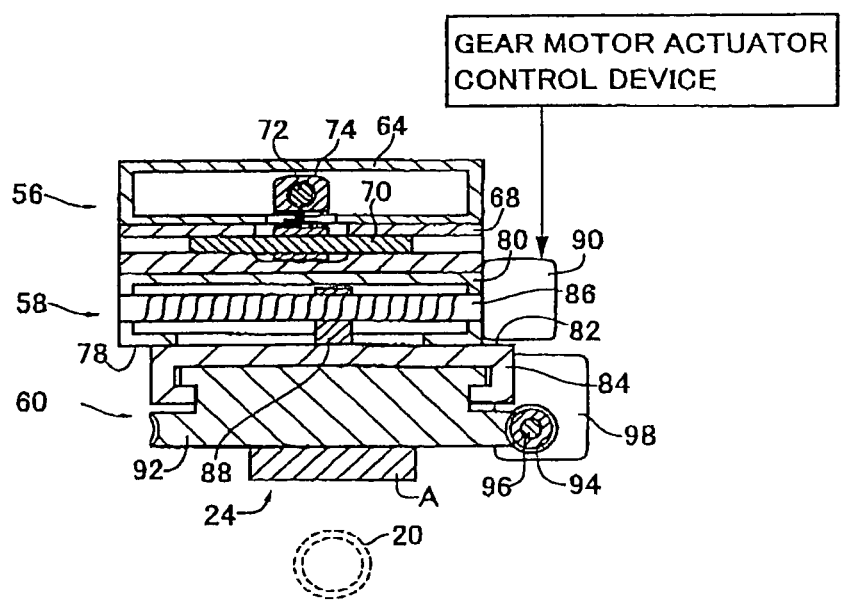
FIG. 6 is a diagram for explaining a state of the ultrasonic probe at the position parallel to the X-axis changed by the X-axis translating mechanism of FIG. 4.

The X-axis rotating mechanism 56 includes a first fixed frame 64 fixed to the unit fixing tool 38 and having a cylindrical sliding concave surface 62 with the center of curvature on the X-axis on the side closer to the ultrasonic probe 24; an X-axis rotating frame 68 having a cylindrical sliding convex surface 66 in a reversed shape of the concavity of the cylindrical sliding concave surface 62 on the side farther from the ultrasonic probe 24 to be in slidable contact with the cylindrical sliding concave surface 62 of the fixed frame 64; a pin 70 fixedly attached to the X-axis rotating frame 68 to be parallel to the X-axis; a first slide member 74 rotatably disposed around the pin 70 at one end and threadably engaged with a first threaded shaft 72 disposed on the first fixed frame 64 at the other end to be parallel to the Y-axis; and an X-axis rotating actuator 76 that rotates the first threaded shaft 72 around the shaft center thereof. The X-axis rotating frame 68 may be rotated when the first slide member 74 coupled thereto is translated in the shaft center direction of the first threaded shaft 72 due to the rotation of the first threaded shaft 72. The ultrasonic probe 24 is positioned in the rotational posture around the X-axis by the X-axis rotating mechanism 56 as depicted in FIG. 5. The X-axis rotating actuator 76 is made up of an electric motor, etc.

The X-axis translating mechanism 58 includes a second fixed frame 80 having the surface farther from the ultrasonic probe 24 fixed to the side of the X-axis rotating frame 68 closer to the ultrasonic probe 24 and having a first sliding flat surface 78 consisting of a flat surface on the opposite side of the fixed surface; an X-axis translating frame 84 having a second sliding flat surface 82 consisting of a flat surface farther from the ultrasonic probe 24 to be in slidable contact with the first sliding flat surface 78 of the second fixed frame 80; a second slide member 88 fixed to the X-axis translating frame 82 at one end and threadably engaged with a second threaded shaft 86 disposed on the second fixed frame 80 at the other end to be parallel to the Y-axis; and an X-axis translating actuator 90 that rotates the second threaded shaft 86 around the shaft center thereof. The X-axis translating frame 82 may linearly be moved in the X-axis direction when the second slide member 88 coupled thereto is translated in the shaft center direction of the first threaded shaft 72 due to the rotation of the first threaded shaft 72. The ultrasonic probe 24 is positioned in the movement posture in the X-axis direction by the X-axis translating mechanism 58 as depicted in FIG. 5. The X-axis translating actuator 90 is made up of an electric motor, etc.

Figure 7:
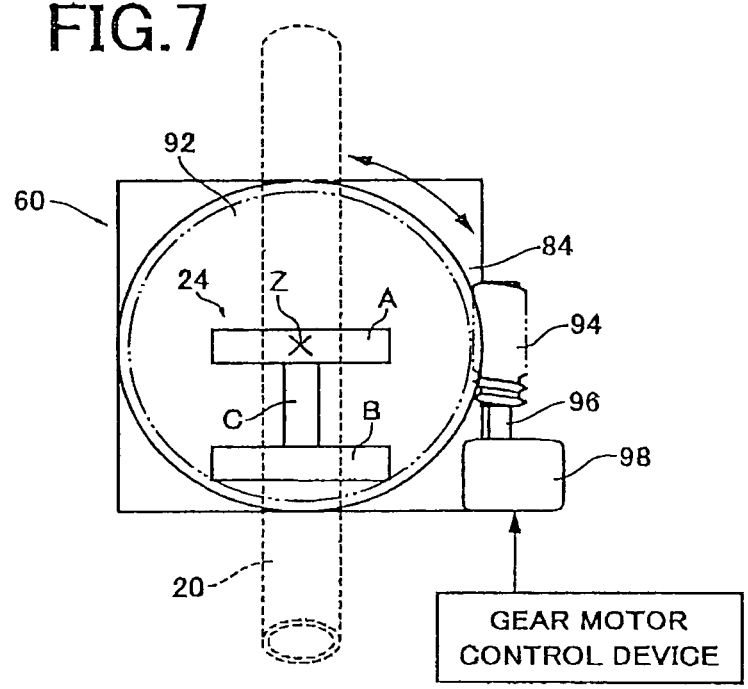
FIG. 7 is a diagram for explaining a configuration of changing the rotational position around the Z-axis of the ultrasonic probe by Z-axis rotating mechanism of FIG. 4.

The Z-axis rotating mechanism 60 includes a worm wheel 92 rotatable held around the Z-axis on the surface of the X-axis translating frame 84 closer to the ultrasonic probe 24 and having the ultrasonic probe 24 fixed on the opposite surface; and an electric motor 98 including a worm gear 94 on an output shaft 96 engaging with circumferential teeth of the worm wheel 92. The ultrasonic probe 24 is positioned in the rotational posture around the Z-axis passing through the longitudinal center portion of the first short axis ultrasonic array probe A by the Z-axis rotating mechanism 60 as depicted in FIG. 7. The electric motor 98 acts as a Z-axis actuator.

Figure 8:
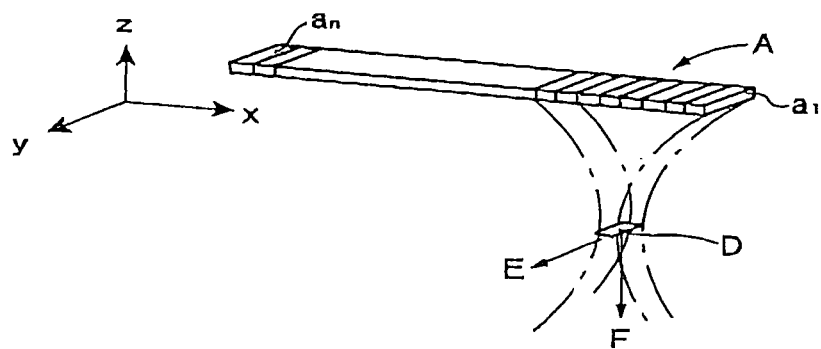
FIG. 8 is a diagram for depicting an ultrasonic beam emitted from an ultrasonic array provided on the ultrasonic probe of FIG. 1 with dashed-dotted lines and explaining a convergent cross section that is a cross section of a convergent portion the ultrasonic beam.
Figure 9:
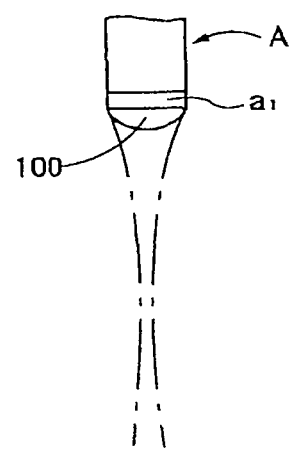
FIG. 9 is a diagram for explaining an acoustic lens provided on the ultrasonic probe of FIG. 1.

In FIG. 1, the ultrasonic drive control circuit 32 performs the beamforming drive by concurrently driving a certain number of the ultrasonic transducers including the ultrasonic transducer $a_1$ at the end, for example, 15 transducers $a_1$ to $a_{15}$ among a plurality of the ultrasonic transducers $a_1$ to $a_n$ arranged in line making up, for example, the first short axis ultrasonic array probe A, at a frequency on the order of 10 MHz with respective phase differences in accordance with instructions from the electronic control device 28 to sequentially emit a convergent ultrasonic beam to the blood vessel 20 in the arrangement direction of the ultrasonic transducers and receives and input to the electronic control device 28 the reflected wave for each emission at the time of scanning (scan) of the ultrasonic beam while the ultrasonic transducers are shifted one by one. Dashed-dotted lines of FIG. 8 represent the convergent ultrasonic beam emitted by the beamforming drive. As depicted in FIG. 9, the emission surface of the first short axis ultrasonic array probe A is provided with an acoustic lens 100 for converge the ultrasonic beam in the direction orthogonal to the arrangement direction of the ultrasonic transducers $a_1$ to $a_n$. The ultrasonic beam made convergent by the beamforming drive and the acoustic lens 100 has a longitudinal-shaped convergent cross section D in the direction orthogonal to the arrangement direction of the ultrasonic transducers $a_1$ to $a_n$ as depicted in FIG. 8. A longitudinal direction E of the convergent cross section D is a direction orthogonal to each of the arrangement direction of the ultrasonic transducers $a_1$ to $a_n$ (X-axis direction) and the beam emitting direction (Z-axis direction) F in plain view, i.e., in the X-Y plane.

The electronic control device 28 synthesizes an image based on the reflected wave to generate and display a cross-section image (short axis image) or a longitudinal-section image (long axis image) of the blood vessel 20 under the skin 18 on the monitor screen displaying device (screen displaying device) 30. The diameter of the blood vessel 20 or the endothelial diameter (lumen diameter), i.e., the diameter of endothelium 101 is calculated from the image. To evaluate the vascular endothelial function, a calculation also made for a change rate of the blood vessel diameter indicative of FMD (flow-mediated dilation) after ischemic reactive hyperemia (%) [=100×(dmax-d)/d] (where d denotes the resting blood vessel diameter and dmax denotes the maximum blood vessel diameter after release of ischemia).

Figure 10:
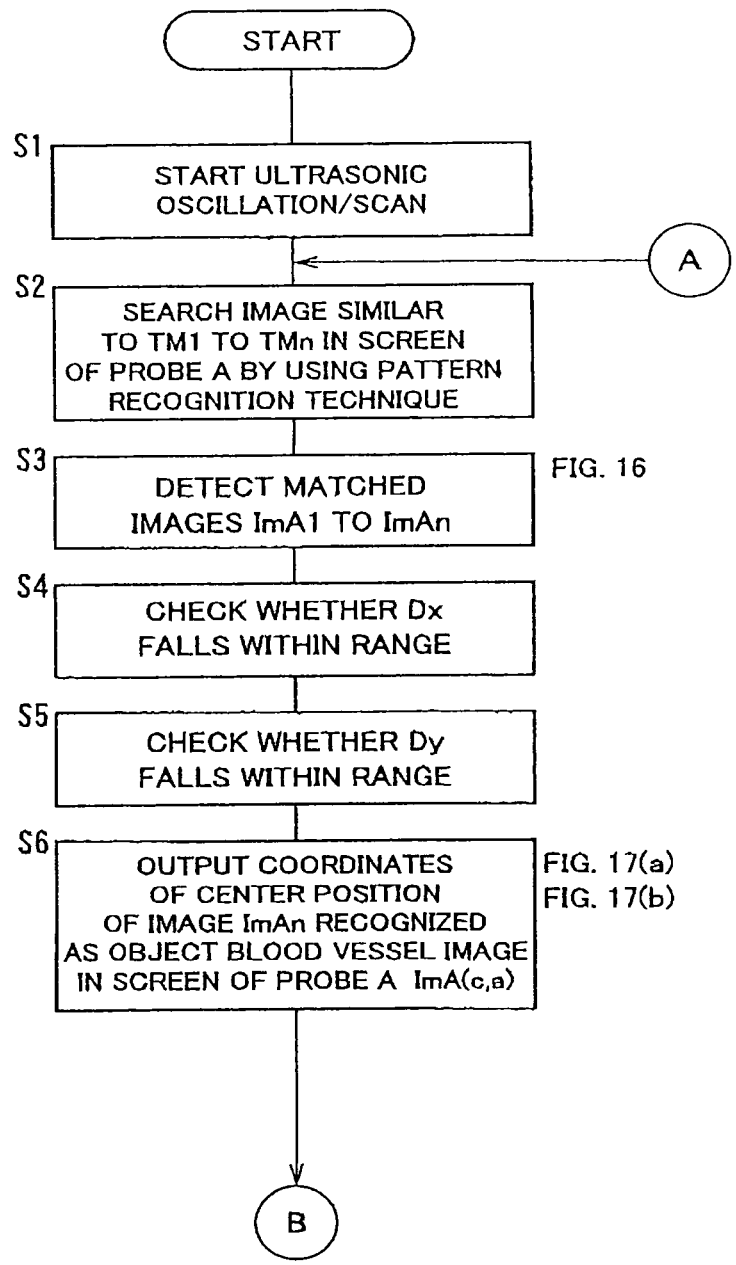
FIG. 10 is a flowchart for explaining a relevant part of control operation for image pattern recognition of a first short axis image display area in an electronic control device of the embodiment of FIG. 1.
Figure 11:
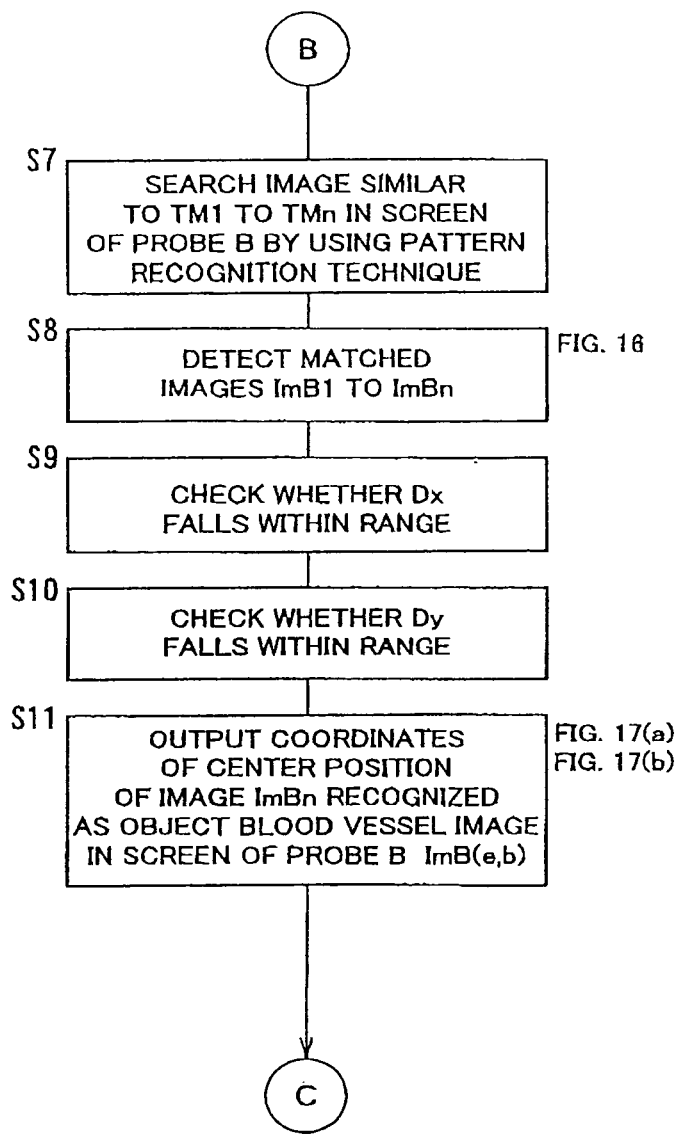
FIG. 11 is a flowchart for explaining a relevant part of the control operation for the image pattern recognition of a second short axis image display area in the electronic control device of the embodiment of FIG. 1.
Figure 15A:
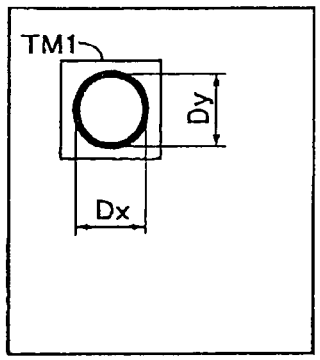
FIG. 15 is a diagram of a standard template registered for performing the image pattern recognition through template matching.
Figure 15B:
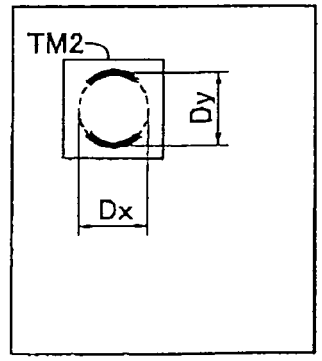
Figure 16:
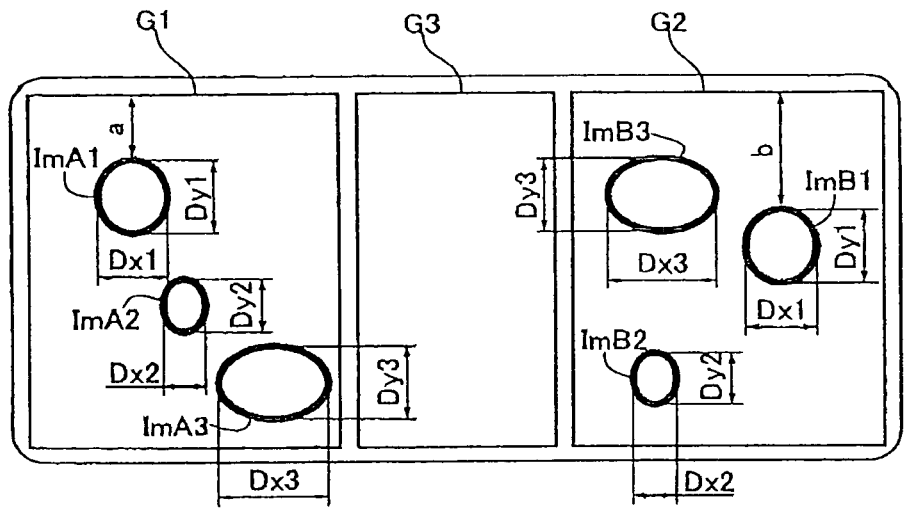
FIG. 16 is a diagram of a display screen of a monitor screen displaying device representing an image pattern detected through the template matching.
Figure 17A:
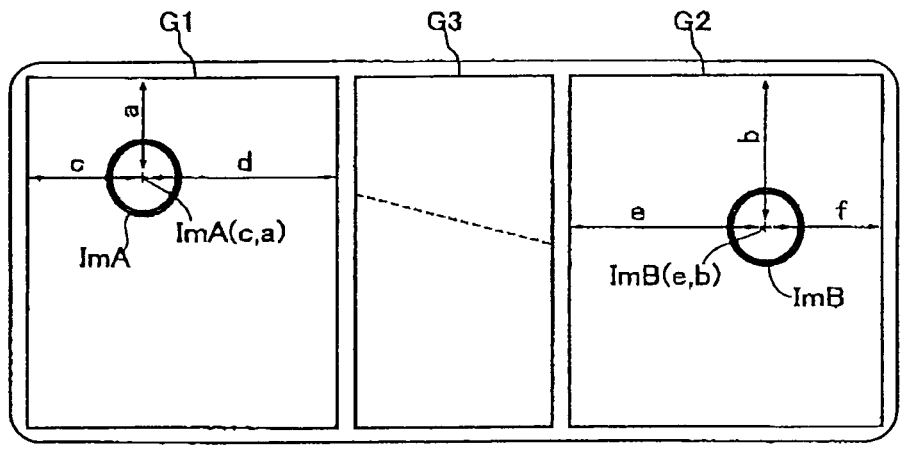
FIG. 17 is a diagram of a relationship between the rotational position around the X-axis of the ultrasonic probe and a cross-section image when the distance from the first short axis ultrasonic array probe to the center of a blood vessel is different from the distance from the second short axis ultrasonic array probe to the center of the blood vessel for explaining the control operation of FIG. 12.
Figure 17B:
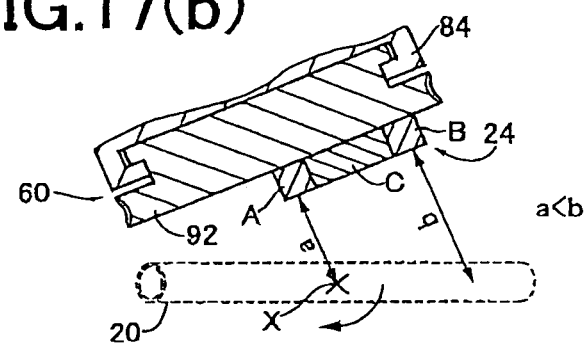

FIGS. 10 to 14 are flowcharts for explaining a relevant part of the control operation of the electronic control device 28. In FIGS. 10 and 11, short axis images TM1 to TMn of typical blood vessels are registered as standard templates in advance to perform the arterial pattern recognition through the template matching technique. Images such as those indicative of the features of the blood vessel to be acquired as an ultrasonic images are registered in advance and, for example, the registration is performed for an image such as TM1 depicted in FIG. 15(*a*) or an image such as TM2 depicted in FIG. 15(*b*) or both TM1 and TM2. In FIG. 10, at step (hereinafter, step is omitted) S1, the ultrasonic oscillation and scanning are started and the convergent ultrasonic beam is emitted from the first short axis ultrasonic array probe A, the second short axis ultrasonic array probe B, and the long axis ultrasonic array probe C and is also scanned. At S2, an image pattern similar to the standard template TM1 is searched by using the template matching technique in the first short axis image display area G1. At S3, matched image patterns ImA1 to ImAn are detected and displayed on the monitor screen displaying device 30. FIG. 16 depicts a display screen of the monitor screen displaying device 30 displaying the detected image patterns ImA1 to ImAn and the display screen is adjacently provided with the first short axis image display area G1 that displays the ultrasonic image from the first short axis ultrasonic array probe A, the long axis image display area G3 that displays the ultrasonic image from the long axis ultrasonic array probe C, and the second short axis image display area G2 that displays the ultrasonic image from the second short axis ultrasonic array probe B in series in a transverse direction. At S4, it is checked whether screen width direction distances Dx1 to Dxn of the detected image patterns ImA1 to ImAn fall within a predetermined range. The predetermined range is preliminarily set to be suitable for a size of an object blood vessel. For example, the range is on the order of 3 to 5 mm in the case of the brachial artery. At S5, it is checked whether screen longitudinal direction distances Dy1 to Dyn of the detected image patterns ImA1 to ImAn fall within a predetermined range. At S6, the image pattern ImAn having Dxn and Dyn falling within the predetermined ranges at S4 and S5 is recognized as an object image pattern ImA of the blood vessel 20 in the first short axis image display area G1 and a coordinate position ImA (c, a) of the center position of the image pattern ImA from the upper side and the left side of the first short axis image display area G1 in a rectangular shape is calculated and output from the image of the display screen of the monitor screen displaying device 30 as depicted in FIG. 17(*a*).

Subsequently, at S7 depicted in FIG. 11, an image pattern similar to the standard template TM1 is searched by using the template matching technique in the second short axis image display area G2. At S8, matched image patterns ImB1 to ImBn are detected. At S9, it is checked whether screen width direction distances Dx1 to Dxn of the detected image patterns ImB1 to ImBn fall within a predetermined range. At S10, it is checked whether screen longitudinal direction distances Dy1 to Dyn of the detected image patterns ImB1 to ImBn fall within a predetermined range. At S11, the image pattern ImBn having Dxn and Dyn falling within the predetermined ranges at S9 and S10 is recognized as an object image pattern ImB of the blood vessel 20 in the second short axis image display area G2 and coordinates ImB (e, b) of the center position of the image pattern ImB from the upper side and the left side of the second short axis image display area G2 in a rectangular shape is calculated and output from the image of the display screen of the monitor screen displaying device 30 as depicted in FIG. 17(*a*).

Figure 12:
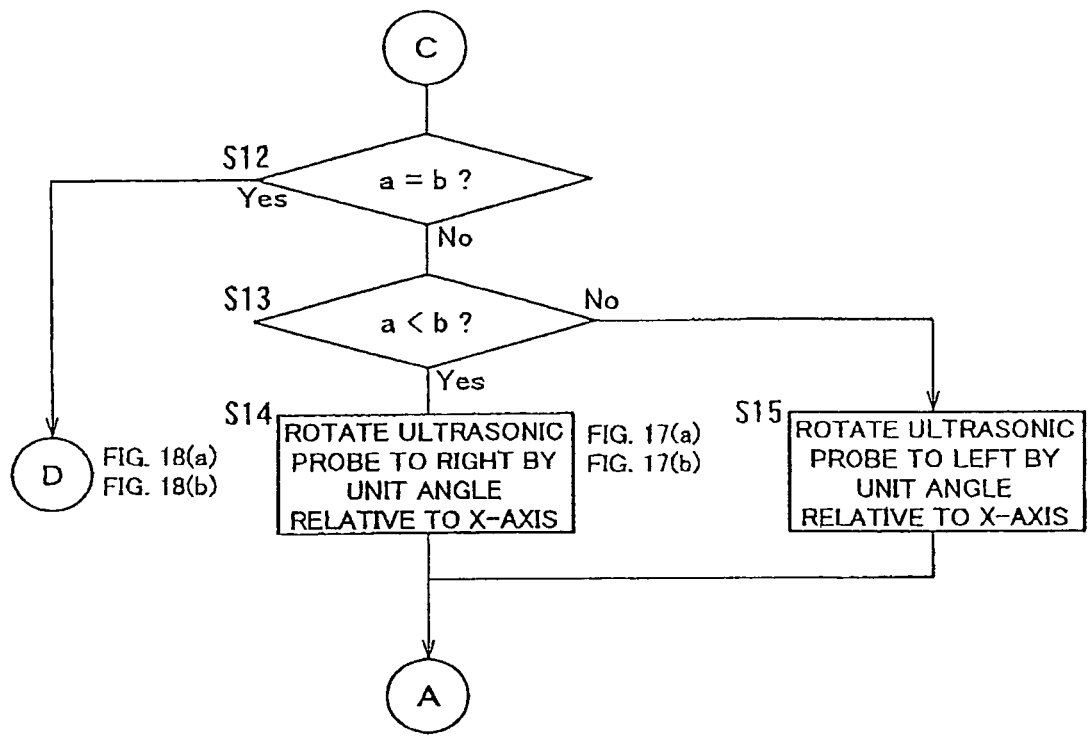
FIG. 12 is a flowchart for explaining an around-X-axis positioning step causing the multiaxis driving device (positioning device) to position the ultrasonic probe around the X-axis such that a distance from a first short axis ultrasonic array probe to the center of a blood vessel becomes equal to a distance from a second short axis ultrasonic array probe to the center of the blood vessel.
Figure 18A:
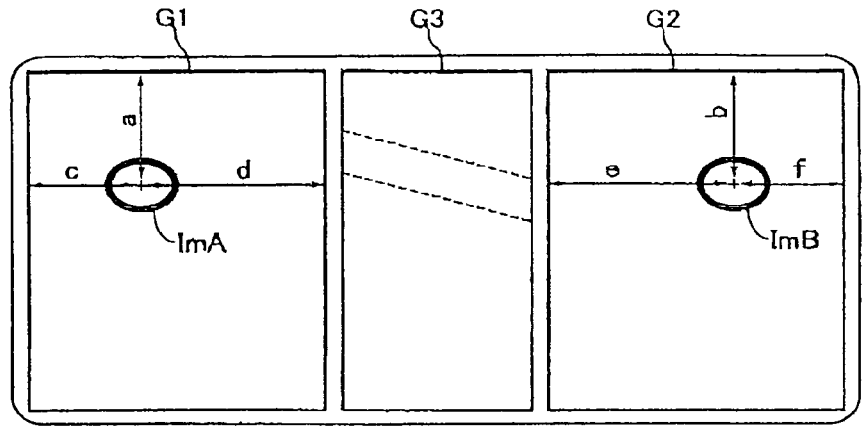
FIG. 18 is a diagram of a relationship between the rotational position around the X-axis of the ultrasonic probe and the cross-section image when the distance from the first short axis ultrasonic array probe to the center of a blood vessel is equal to the distance from the second short axis ultrasonic array probe to the center of the blood vessel for explaining the control operation of FIG. 12.
Figure 18B:
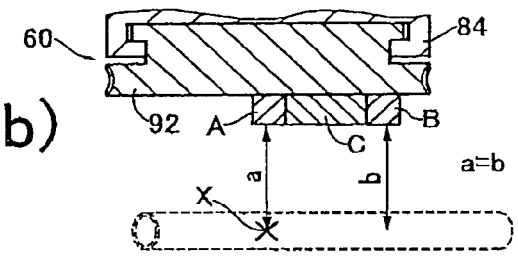

Subsequently, at S12 of FIG. 12, it is determined whether a indicative of the coordinate position in the longitudinal direction of the blood vessel in G1 is identical to b in G2. As depicted in FIGS. 17(*b*) and 18(*b*), a and b also denote values indicative of the distances from the first short axis ultrasonic array probe A and the second short axis ultrasonic array probe B to the center of the blood vessel 20. If the determination at S12 is negative, it is determined at S13 whether a is smaller than b. If the determination at S13 is positive, the ultrasonic probe 24 is rotated to the right by a predetermined angle relative to the X-axis by the X-axis rotating actuator 76 at S14 as depicted in FIG. 17(*b*) and, if the determination is negative, the ultrasonic probe 24 is rotated to the left by a predetermined angle relative to the X-axis by the X-axis rotating actuator 76 at S15. The predetermined angle is a slight amount of angle set in advance and corresponds to a unit angle. The determination at S12 is positive when the distance a from the first short axis ultrasonic array probe A to the center of the blood vessel 20 is equal to the distance b from the second short axis ultrasonic array probe B to the center of the blood vessel 20 as depicted in FIGS. 18(*b*) and S13 to S15 and S2 to S12 are repeatedly executed in sequence while the positive determination is not made. S2 to S15 correspond to an around-X-axis positioning step of causing the multiaxis driving device (positioning device) 26 to position the ultrasonic probe 24 around the X-axis such that the distance from the first short axis ultrasonic array probe A to the center of the blood vessel 20 becomes equal to the distance from the second short axis ultrasonic array probe B to the center of the blood vessel 20.

Figure 13:
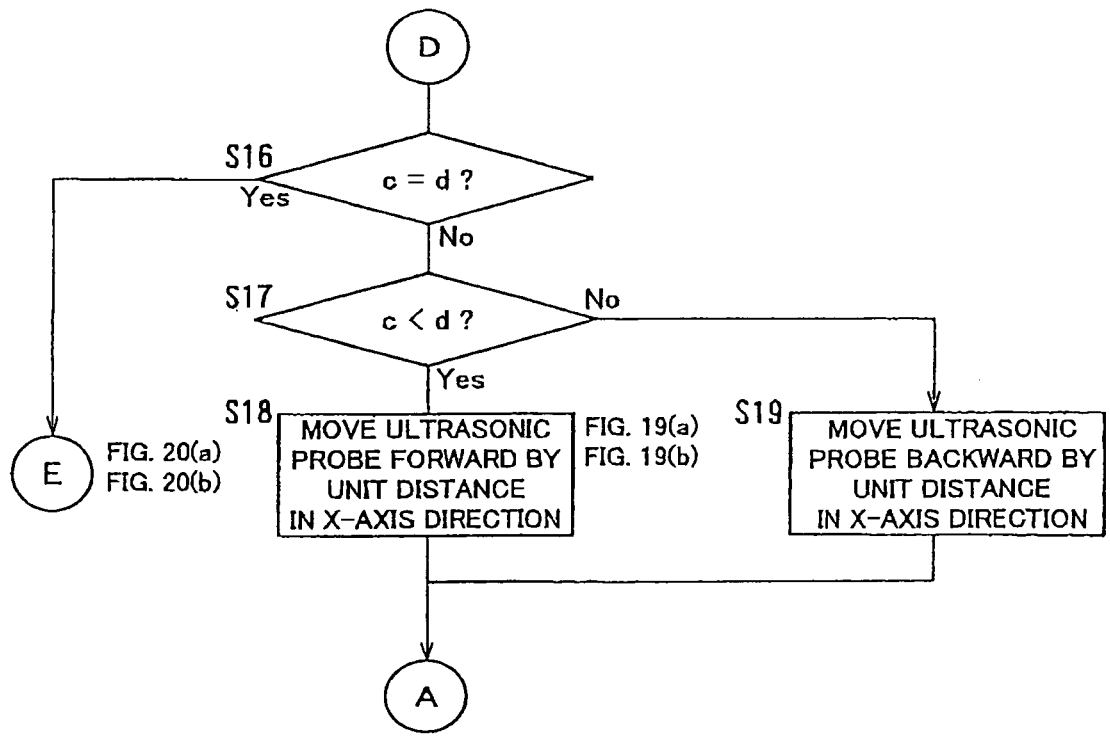
FIG. 13 is a flowchart for explaining the X-axis direction positioning causing the multiaxis driving device (positioning device) to translate the ultrasonic probe in the X-axis direction such that an image of the blood vessel is located at the center of the width direction of the first short axis image display area.
Figure 19A:
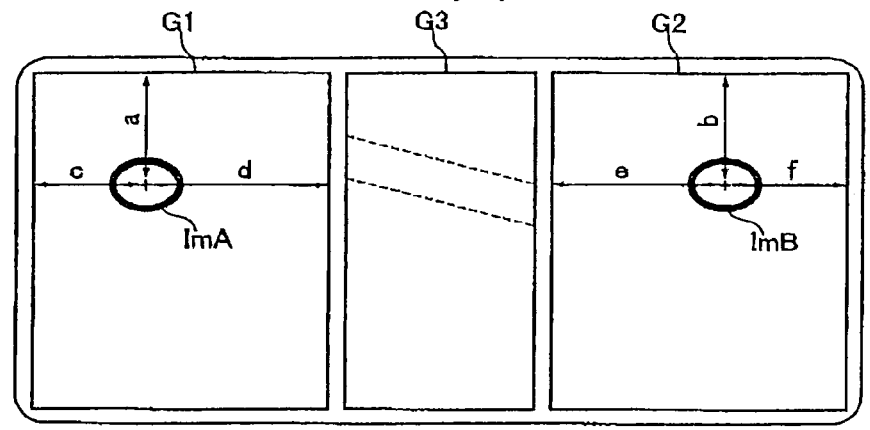
FIG. 19 is a diagram of a relationship between the translational position in the X-axis direction of the ultrasonic probe and the cross-section image when the first short axis ultrasonic array probe intersects with the blood vessel in the directional view orthogonal to the X-Y plane for explaining the control operation of FIG. 13.
Figure 19B:
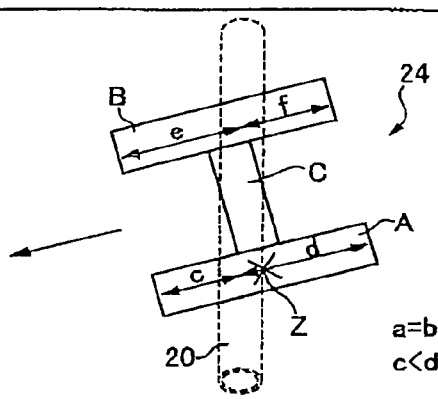
Figure 20A:
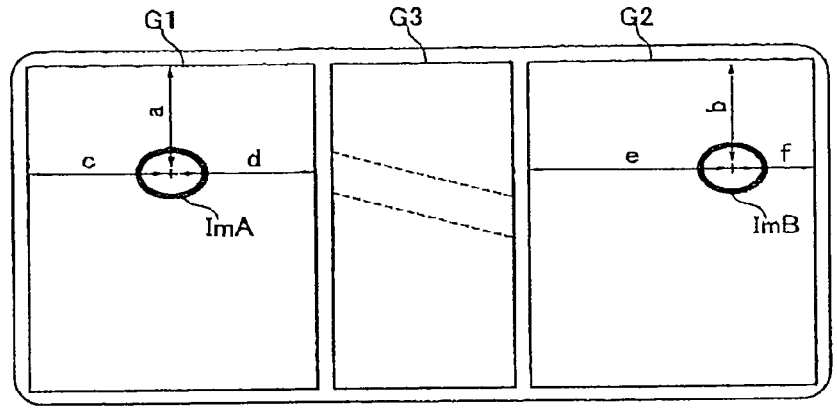
FIG. 20 is a diagram of a relationship between the translational position in the X-axis direction of the ultrasonic probe and the cross-section image when the intersecting point between the first short axis ultrasonic array probe and the blood vessel comes to coincide with the Z-axis in the directional view orthogonal to the X-Y plane for explaining the control operation of FIG. 13.
Figure 20B:
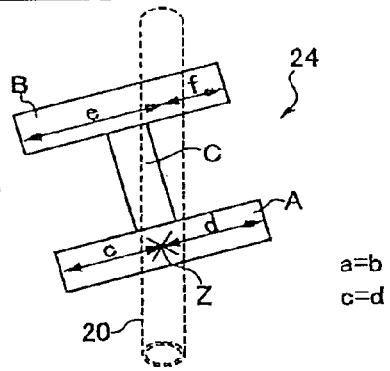

Subsequently, in FIG. 13, if the determination at S12 is positive, it is determined at S16 whether c indicative of the coordinate position in the longitudinal direction of the blood vessel in G1 is identical to d in G2. As depicted in FIGS. 19(*b*) and 20(*b*), c and d denote values corresponding to the distance from one end in the longitudinal direction of the first short axis ultrasonic array probe A to the intersecting point with the longitudinal center of the blood vessel 20 and the distance from the other end in the longitudinal direction of the first short axis ultrasonic array probe A to the intersecting point with the longitudinal center of the blood vessel 20 in the directional view orthogonal to the X-Y plane. If the determination at S16 is negative, it is determined at S17 whether c is smaller than d. If the determination at S17 is positive, the ultrasonic probe 24 is moved forward by a predetermined distance in the X-axis direction (direction of an arrow in FIG. 19(*b*)) by the X-axis translating actuator 90 at S17 as depicted in FIG. 19(*b*) and, if the determination is negative, the ultrasonic probe 24 is moved backward by a predetermined distance in the X-axis direction (opposite direction of the arrow in FIG. 19(*b*)) by the X-axis translating actuator 90 at S19. The predetermined distance is a slight amount of distance set in advance and corresponds to a unit distance. The determination at S16 is positive when the intersecting point between the first short axis ultrasonic array probe A and the blood vessel 20 conforms to the Z-axis in the directional view orthogonal to the X-Y plane as depicted in FIGS. 20(*b*) and S17 to S19, S2 to S12, and S16 are repeatedly executed in sequence while the positive determination is not made. S2 to S12 and S16 to S19 correspond to an X-axis direction positioning step of causing the multiaxis driving device (positioning device) 26 to translate the ultrasonic probe 24 in the X-axis direction such that the image of the blood vessel 20 is positioned at the center portion in the width direction of the first short axis image display area G1.

Figure 14:
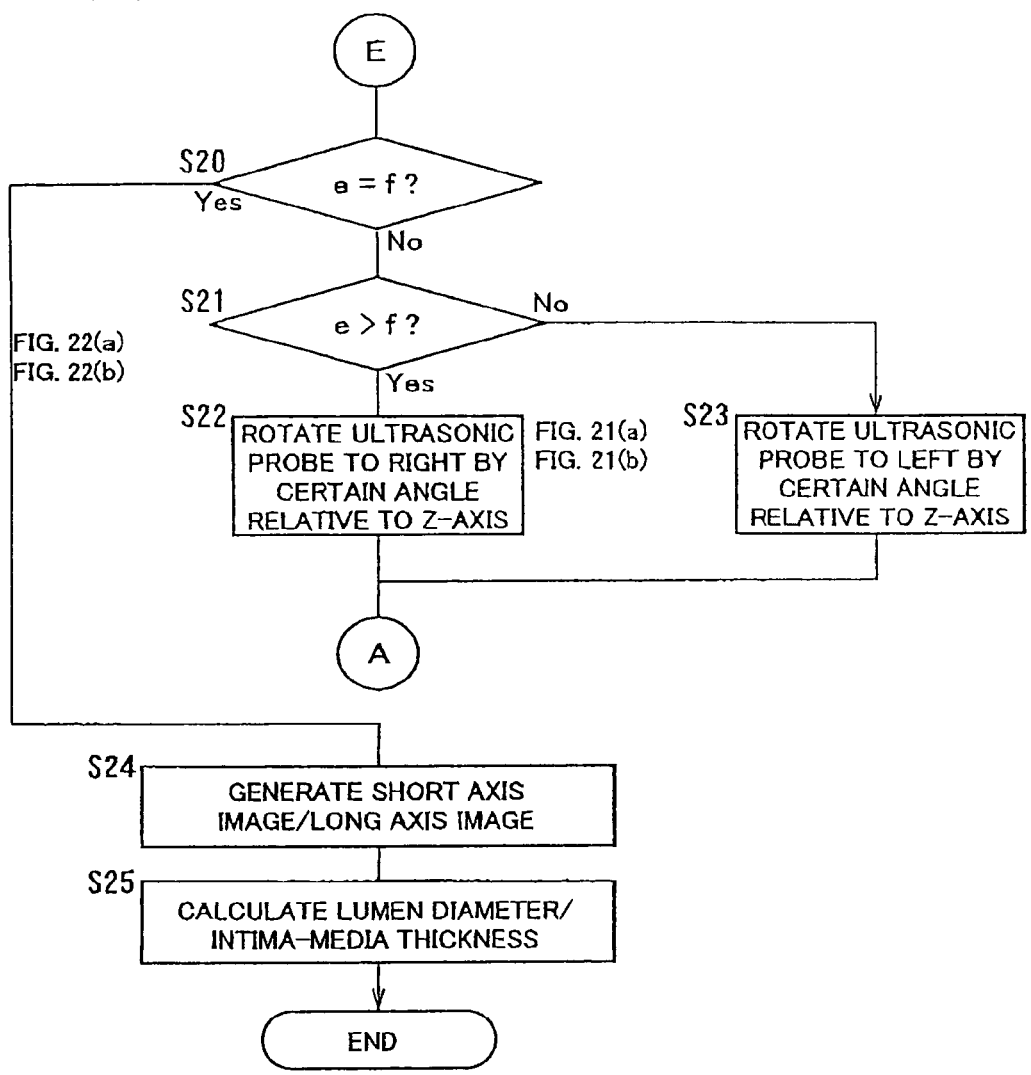
FIG. 14 is a flowchart for explaining an around-Z-axis positioning step causing the multiaxis driving device (positioning device) to rotate around the Z-axis such that the image of the blood vessel is located at the center of the width direction of the second short axis image display area.
Figure 21A:
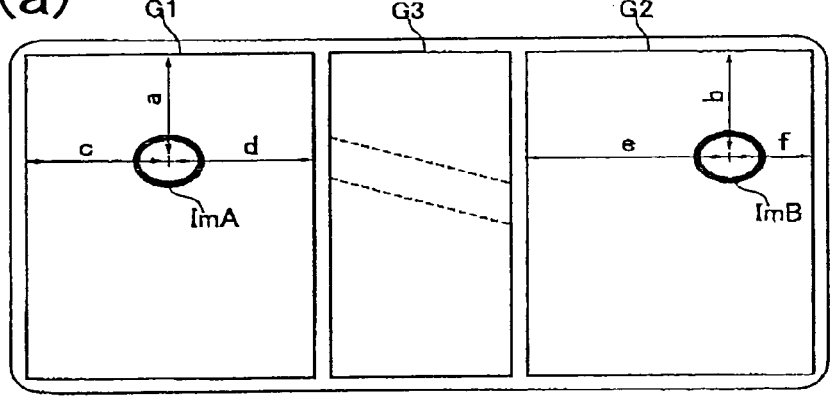
FIG. 21 is a diagram of a relationship between the rotational position around the Z-axis of the ultrasonic probe and the cross-section image when the first short axis ultrasonic array probe and the second short axis ultrasonic array probe is not orthogonal to the blood vessel in the directional view orthogonal to the X-Y plane for explaining the control operation of FIG. 14.
Figure 21B:
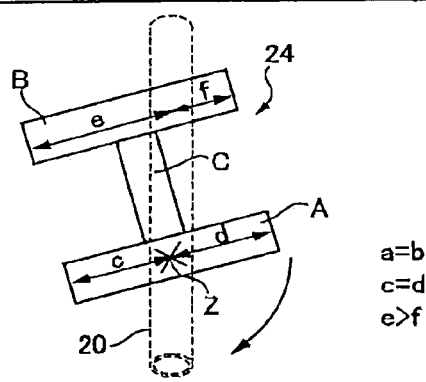
Figure 22A:
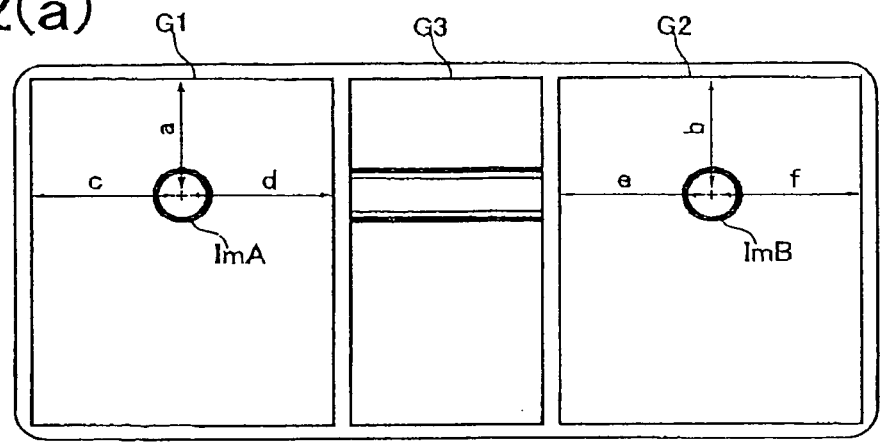
FIG. 22 is a diagram of a relationship between the rotational position around the Z-axis of the ultrasonic probe and the cross-section image when the first short axis ultrasonic array probe and the second short axis ultrasonic array probe is orthogonal to the blood vessel in the directional view orthogonal to the X-Y plane for explaining the control operation of FIG. 14.
Figure 22B:
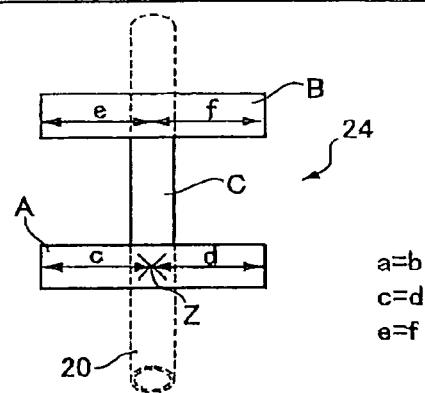

Subsequently, in FIG. 14, if the determination at S16 is positive, it is determined at S20 whether e and f are identical. As depicted in FIGS. 21(*b*) and 22(*b*), e and f denote values corresponding to the distance from one end in the longitudinal direction of the second short axis ultrasonic array probe B to the intersecting point with the longitudinal center of the blood vessel 20 and the distance from the other end in the longitudinal direction of the second short axis ultrasonic array probe B to the intersecting point with the longitudinal center of the blood vessel 20 in the directional view orthogonal to the X-Y plane. If the determination at S20 is negative, it is determined at S21 whether e is greater than f. If the determination at S21 is positive, the ultrasonic probe 24 is rotated to the right by a predetermined angle relative to the Z-axis by the electric motor 98 at S22 as depicted in FIG. 21(*b*) and, if the determination is negative, the ultrasonic probe 24 is rotated to the left by a predetermined angle relative to the Z-axis by the electric motor 98 at S23. The predetermined angle is a slight amount of angle set in advance and corresponds to a unit angle for the positioning operation. The determination at S20 is positive when the first short axis ultrasonic array probe and the second short axis ultrasonic array probe is orthogonal to the blood vessel in the directional view orthogonal to the X-Y plane as depicted in FIGS. 22(*b*) and S21 to S23, S2 to S12, S16, and S20 are repeatedly executed in sequence while the positive determination is not made. S2 to S12, S16, and S20 correspond to an around-Z-axis positioning step of causing the multiaxis driving device (positioning device) 26 to rotate around the Z-axis such that the image of the blood vessel 20 is positioned at the center portion in the width direction of the second short axis image display area G2.

Figure 23:
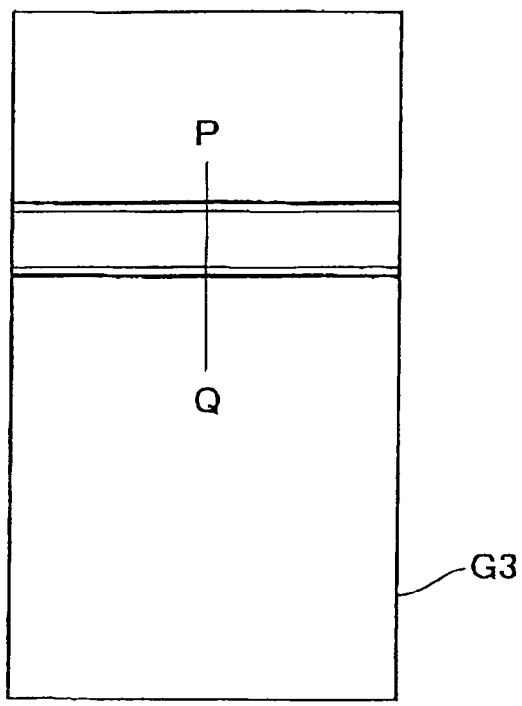
FIG. 23 is a diagram of a long axis image display area that displays an ultrasonic image from a long axis ultrasonic array probe of FIG. 22.
Figure 24:
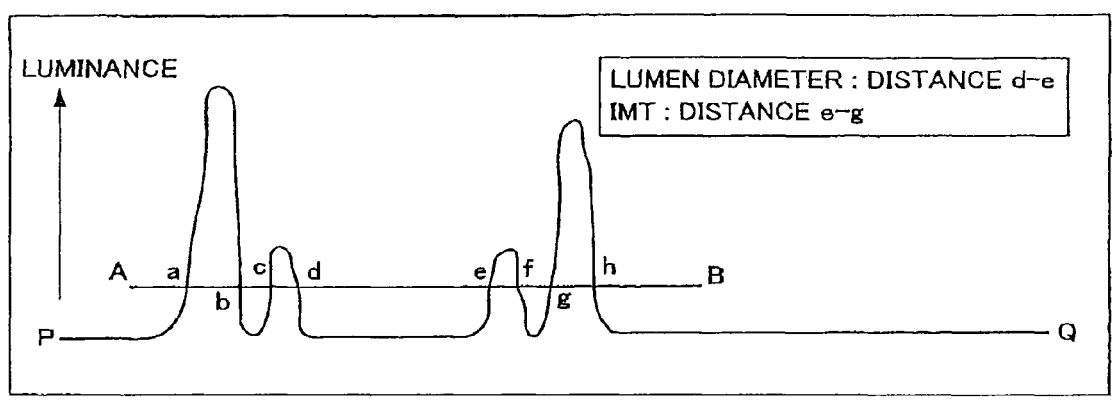
FIG. 24 is a line profile indicative of an extent of the screen luminance on a line P-Q of the long axis image display area of FIG. 23.

Subsequently, at S24, the sectional images of the blood vessels 20, i.e., the short axis image and the long axis image are generated, displayed on the monitor screen displaying device 30, and stored, and at S25, the lumen diameter (endothelial diameter), the intima thickness, and the intima-media thickness, etc., are automatically calculated by the display control portion of the electronic control device 28. FIG. 23 is a diagram of the long axis image display area G3 that displays an ultrasonic image from the long axis ultrasonic array probe C of FIG. 22 and FIG. 24 is a line profile indicative of the screen luminance, i.e., the intensity of the ultrasonic reflection signal, on a line P-Q near the center of the long axis image display area of FIG. 23. In FIG. 24, the lumen diameter of the blood vessel 20 is calculated as a distance d-e, which is the largest intersecting point distance acquired by calculating respecting intersecting point distances at points of an intersecting point a to an intersecting point h acquired by drawing a reference line A-B such that eight intersecting points are detected on a predetermined luminance determination line. Although the intima thickness, etc., are calculated by using the points from the intersecting point a to the intersecting point h from which the largest distance d-e is acquired, a distance e-g, i.e., a distance between the intersecting point e and the intersecting point g is particularly referred to as the intima-media thickness (IMT) and the measured value is used as an index of determination of arterial sclerosis. S25 corresponds to a blood vessel diameter calculating step of calculating the lumen diameter of the blood vessel 20 based on the long axis image signal of the blood vessel 20 detected by the long axis ultrasonic array probe C and a blood vessel membrane thickness calculating step of calculating the intima thickness and/or the intima-media thickness of the blood vessel 20 based on the long axis image signal of the blood vessel 20 detected by the long axis ultrasonic array probe C.

As above, since the blood vessel ultrasonic image measuring method of this embodiment includes (d) the around-X-axis positioning step of causing the multiaxis driving device (positioning device) 26 to position the ultrasonic probe 24 around the X-axis such that the distance a from the first short axis ultrasonic array probe A to the center of the blood vessel 20 becomes equal to the distance b from the second short axis ultrasonic array probe B to the center of the blood vessel 20, (e) the X-axis direction positioning step of causing the multiaxis driving device (positioning device) 26 to translate the ultrasonic probe 24 in the X-axis direction such that the image of the blood vessel 20 is positioned at the center portion in the width direction of the first short axis image display area G1, and (f) the around-Z-axis positioning step of causing the multiaxis driving device (positioning device) 26 to rotate the ultrasonic probe 24 around the Z-axis such that the image of the blood vessel 20 is positioned at the center portion in the width direction of the second short axis image display area G2, the positioning may be performed by using the positions in the longitudinal direction of the ultrasonic array probes relative to the blood vessel 20 or the distances of the ultrasonic array probes to the blood vessel 20 and, therefore, the ultrasonic probe 24 may simply and easily be positioned on the blood vessel 20 of the living body 14 with higher accuracy.

According to the blood vessel ultrasonic image measuring method of this embodiment, since the X-axis is an axis passing under the skin 18, i.e., through or in the vicinity of the blood vessel 20, and the around-X-axis positioning step is a step of positioning the ultrasonic probe 24 around the X-axis, the condition of pressing the skin 18 by the first short axis ultrasonic array probe A and the second short axis ultrasonic array probe B may not significantly be changed to change the distances between the probes and the blood vessel 20. Since the X-axis is located immediately under the first short axis ultrasonic array probe in this embodiment, almost no change is made in the condition of pressing the skin 18 by the first short axis ultrasonic array probe A and the distance between the first short axis ultrasonic array probe A and the blood vessel 20.

According to the blood vessel ultrasonic image measuring method of this embodiment, the ultrasonic probe 24 includes the long axis ultrasonic array probe C having a plurality of ultrasonic transducers (ultrasonic oscillators) $a_1$ to $a_n$ in the Y-axis direction orthogonal to the X-axis between the first short axis ultrasonic array probe A and the second short axis ultrasonic array probe B, i.e., adjacent to the first short axis ultrasonic array probe A and the second short axis ultrasonic array probe B, on the X-Y plane that is the one flat surface; the Z-axis is a direction passing through the intersecting point between the longitudinal direction of the first short axis ultrasonic array probe A and the longitudinal direction of the long axis ultrasonic array probe C and orthogonal to the X-axis direction and the Y-axis direction; (k) the monitor screen displaying device (image displaying device) 30 includes the long axis image display area G3 that displays the ultrasonic image from the long axis ultrasonic array probe C between the first short axis image display area G1 and the second short axis image display area G2, i.e., adjacent to the first short axis image display area G1 and the second short axis image display area G2; the first short axis image display area G1, the second short axis image display area G2, and the long axis image display area G3 include a common longitudinal axis indicative of a depth dimension from the skin 18; and therefore the long axis ultrasonic array probe C is preferably positioned on the center of the blood vessel 20.

Since the blood vessel ultrasonic image measuring method of this embodiment includes the blood vessel diameter calculating step of calculating the lumen diameter of the blood vessel 20 based on the long axis image signal of the blood vessel 20 detected by the long axis ultrasonic array probe C, the blood vessel diameter may accurately be acquired.

Since the blood vessel ultrasonic image measuring method of this embodiment includes the blood vessel membrane thickness calculating step of calculating the intima thickness and the intima-media thickness of the blood vessel 20 based on the long axis image signal of the blood vessel 20 detected by the long axis ultrasonic array probe C, the intima thickness and the intima-media thickness of the blood vessel may accurately be acquired.

According to the blood vessel ultrasonic image measuring method of this embodiment, since the pattern recognition is performed for recognizing the image of the blood vessel 20 at the around-X-axis positioning step, the X-axis direction positioning step, or the around-Z-axis positioning step, the ultrasonic probe 24 may simply and easily be positioned on the blood vessel 20 of the living body 14 with higher accuracy. Since the template patching technique is used for the pattern recognition, this embodiment is simplified and enables rapid arithmetic processes as compared to the case of using other pattern recognition techniques, for example, the NN (nearest neighbor) technique or the K-means technique.

Second Embodiment

Another embodiment of the present invention will then be described. In the description of the following embodiment, the portions overlapping with the embodiment are denoted by the same reference numerals and will not be described.

Figure 25A:
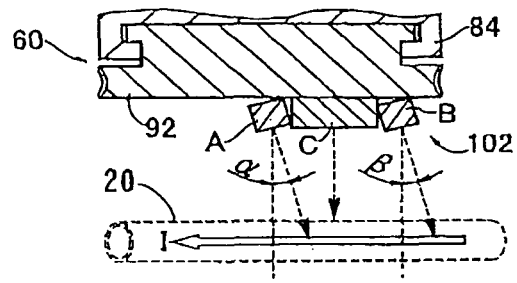
FIG. 25 is a diagram for explaining a configuration of the ultrasonic probe and a monitor screen display of the blood vessel ultrasonic image measuring apparatus in another embodiment of the present invention.
Figure 25B:
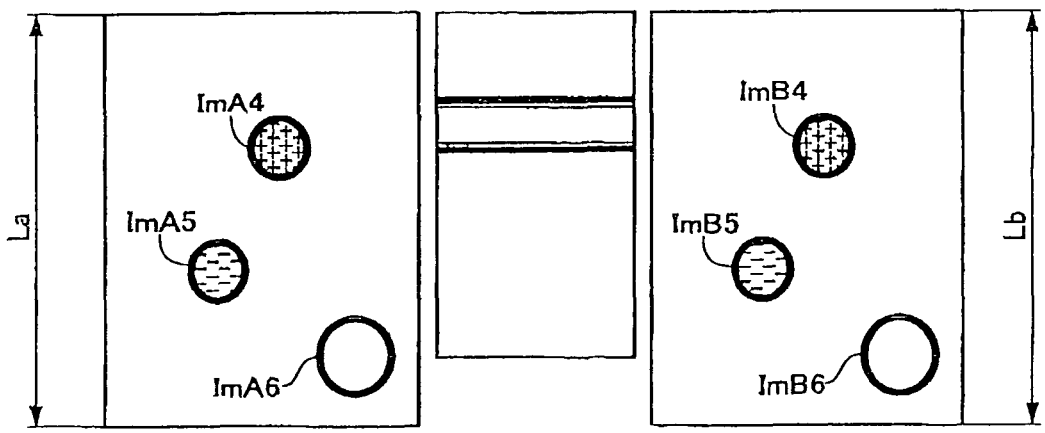
Figure 25C:
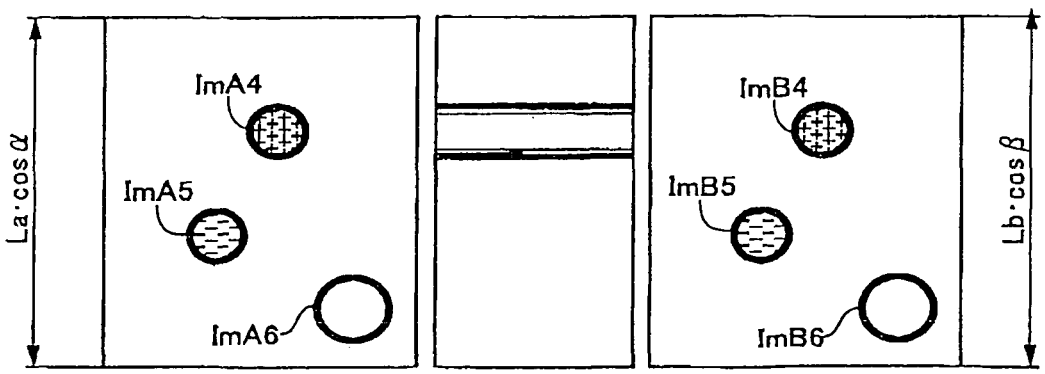

FIG. 25 is a diagram for explaining exemplary configurations of the ultrasonic probe and the monitor screen display in another embodiment of the present invention. The hybrid probe unit 12 of this embodiment includes an H-shaped ultrasonic probe 102 made up of two lines of the first short axis ultrasonic array probe A and the second short axis ultrasonic array probe B parallel to each other and rotated around the X-axis such that directions F orthogonal to the ultrasonic emitting surfaces of the ultrasonic transducers $a_1$ to $a_n$ configured by linear arrangement in the X-axis direction are respectively tilted by predetermined angle $\alpha$ and angle $\beta$ relative to the Z-axis; and the long axis ultrasonic array probe C configured by linearly arranging the ultrasonic transducers (ultrasonic oscillators) $a_1$ to $a_n$ in the Y-axis direction and linking the longitudinal center potions of the first short axis ultrasonic array probe A and the second short axis ultrasonic array probe B on one flat surface. The first short axis ultrasonic array probe A and the second short axis ultrasonic array probe B emits ultrasonic obliquely at the predetermined angle $\alpha$ and angle $\beta$ in directions toward the upstream of the blood vessel 20 to the blood vessel 20 in the blood flowing state in the direction of an arrow I of FIG. 25(a).

FIG. 25(b) depicts a display screen of the monitor screen displaying device 30 when an image generated based on the reflected wave acquired by the ultrasonic probe 102 with the configuration is displayed without performing special conversion. As compared to the state when the ultrasonic emission direction of the first short axis ultrasonic array probe A and the second short axis ultrasonic array probe B is orthogonal to the blood vessel 20, the longitudinal direction of the image is increased by factors of ($1/\cos \alpha$) and ($1/\cos \beta$) in the display. The first short axis image display area G1, the second short axis image display area G2, and the long axis image display area G3 have no common longitudinal axis indicative of a depth dimension from the skin 18. In FIG. 25, when the respectively detected short axis ultrasonic images of the blood vessel 20 are displayed in the first short axis image display area G1 and the second short axis image display area G2, the short axis ultrasonic images respectively displayed in the first short axis image display area G1 and the second short axis image display area G2 are reduced on the display screen through an arithmetic step of factors of $\cos \alpha$ and $\cos \beta$ in the screen longitudinal direction. This arithmetic step corresponds to an image correcting step of correcting the short axis ultrasonic images respectively displayed in the first short axis image display area G1 and the second short axis image display area G2 based on the predetermined angle $\alpha$ and angle $\beta$ to form images in the state that the ultrasonic emission direction of the first short axis ultrasonic array probe A and the second short axis ultrasonic array probe B is orthogonal to the blood vessel 20. A color display forming step is also performed to convert the images such that the blood vessel 20 is represented by colors corresponding to the blood flowing direction and this facilitates automatic identification and visual identification of arteries. The arithmetic step and the color display forming step are automatically executed by the display control portion of the electronic control device 28 depicted in FIG. 1 when the ultrasonic images are generated and the display is performed on the monitor screen displaying device 30.

As above, according to the blood vessel ultrasonic image measuring method of this embodiment, since the first short axis ultrasonic array probe A and the second short axis ultrasonic array probe B emits ultrasonic obliquely at the predetermined angles to the blood vessel 20 in directions toward the upstream of the blood vessel 20, the blood flow velocity becomes measurable with the ultrasound Doppler.

Since the blood vessel ultrasonic image measuring method of this embodiment includes the image correcting step of correcting the short axis ultrasonic images respectively displayed in the first short axis image display area G1 and the second short axis image display area G2 based on the predetermined angles to form images in the state that the ultrasonic emission direction of the first short axis ultrasonic array probe A and the second short axis ultrasonic array probe B is orthogonal to the blood vessel 20 when the short axis ultrasonic images of the blood vessel 20 respectively detected by the first short axis ultrasonic array probe A and the second short axis ultrasonic array probe B are respectively displayed in the first short axis image display area G1 and the second short axis image display area G2, the blood flow velocity becomes measurable with the ultrasound Doppler and the short axis ultrasonic images respectively displayed in the first short axis image display area G1 and the second short axis image display area G2 are formed as accurate cross-section images.

Third Embodiment

Figure 26:
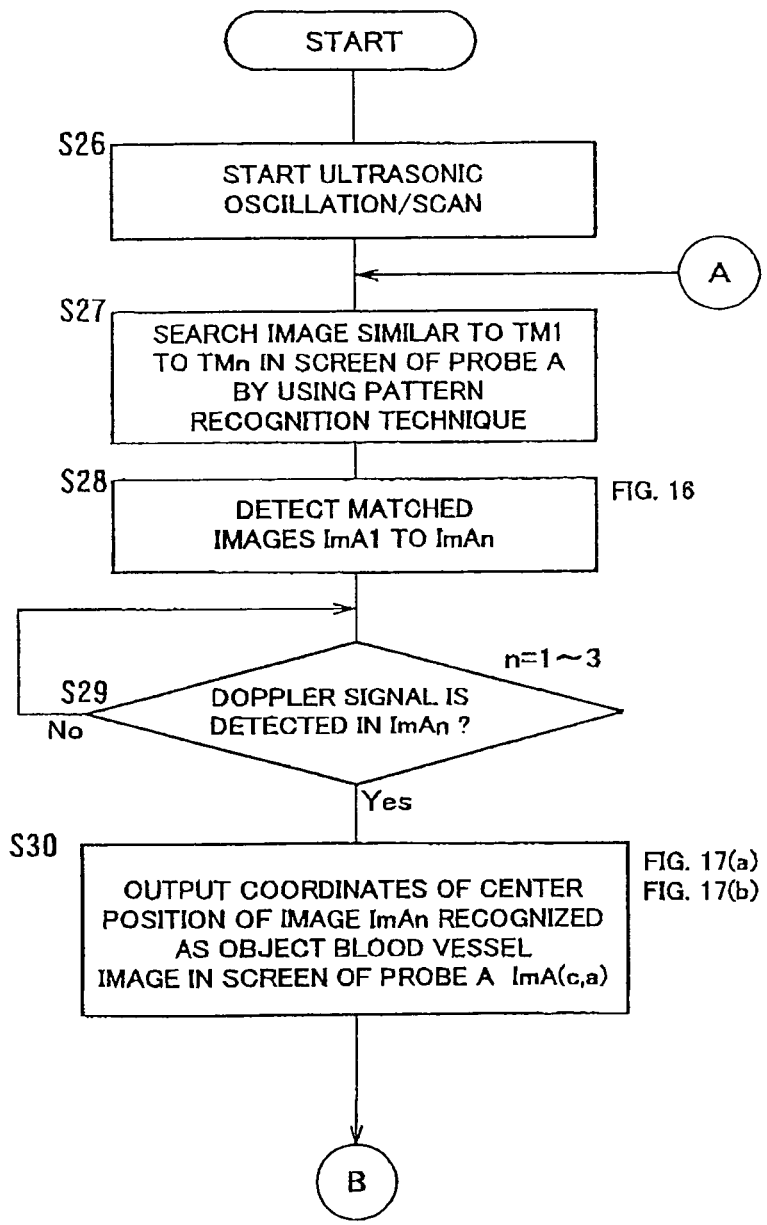
FIG. 26 is a flowchart for explaining a relevant part of the control operation for the image pattern recognition of the first short axis image display area in an electronic control device including a Doppler signal processing portion in another embodiment of the present invention, corresponding to FIG. 10.
Figure 27:
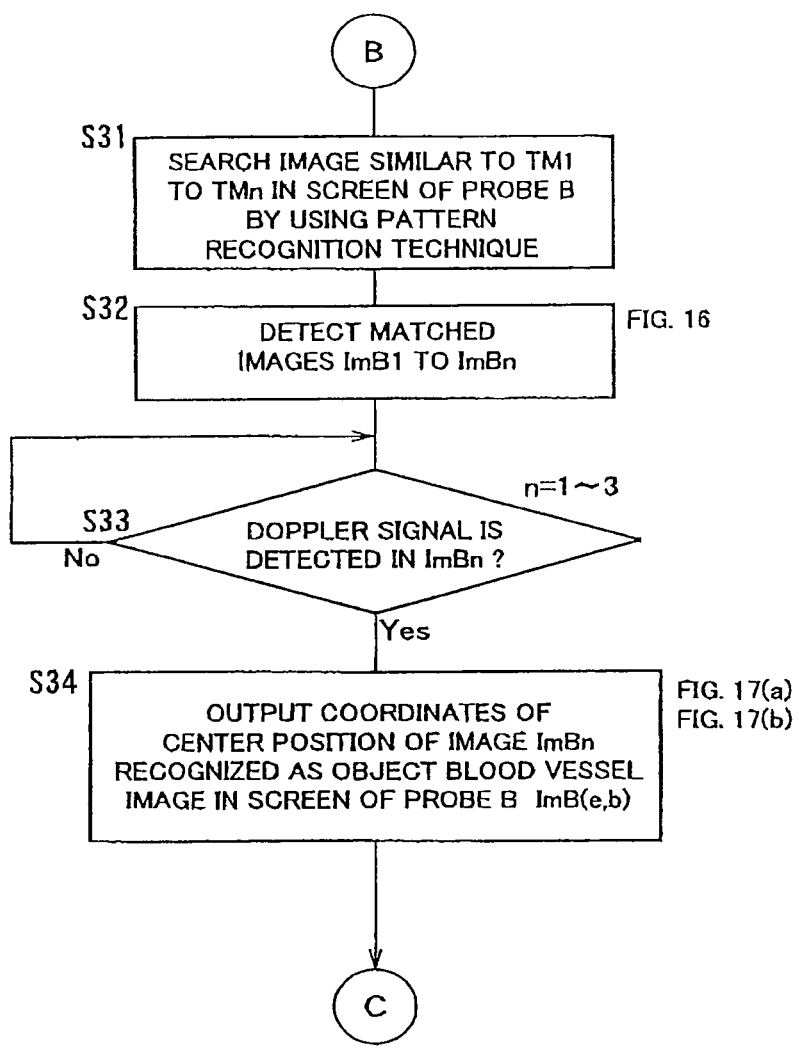
FIG. 27 is a flowchart for explaining a relevant part of the control operation for the image pattern recognition of the second short axis image display area in the electronic control device including the Doppler signal processing portion in another embodiment of the present invention, corresponding to FIG. 11.

FIGS. 26 and 27 are flowcharts for explaining a portion of a relevant part of the control operation of the electronic control device 28 in another embodiment of the present invention. Although the artery pattern recognition is performed at steps depicted in the flowcharts of FIGS. 10 and 11 in the embodiment, if the electronic control device 28 includes a Doppler signal processing portion, the artery pattern recognition is performed at steps depicted in the flowcharts of FIGS. 26 and 27 instead of FIGS. 10 and 11. In FIG. 26, at step S26, the ultrasonic oscillation and scanning are started and the convergent ultrasonic beam is emitted from the first short axis ultrasonic array probe A, the second short axis ultrasonic array probe B, and the long axis ultrasonic array probe C and is also scanned. At step S27, an image pattern similar to the standard template TM1 is searched by using the template matching technique in the first short axis image display area G1. At S28, the matched image patterns ImA1 to ImAn are detected and displayed on the monitor screen displaying device 30. At S29, it is determined whether a Doppler signal is detected from the detected image patterns ImA1 to ImAn (n=3 in this embodiment). At S30, the image pattern ImAn with the positive determination at step S29 is recognized as the object image pattern ImA of the blood vessel 20 in the first short axis image display area G1 and the coordinates ImA (c, a) of the center position of the image pattern ImA from the upper side and the left side of the first short axis image display area G1 in a rectangular shape is calculated and output.

Subsequently, in FIG. 27, at S31, an image pattern similar to the standard template TM1 is searched by using the template matching technique in the second short axis image display area G2. At S32, the matched image patterns ImB1 to ImBn are detected and displayed on the monitor screen displaying device 30. At S33, it is determined whether a Doppler signal is detected from the detected image patterns ImB1 to ImBn (n=3 in this embodiment). At S34, the image pattern ImAn with the positive determination at step S33 is recognized as the object image pattern ImB of the blood vessel 20 in the first short axis image display area G1 and the coordinates ImB (e, b) of the center position of the image pattern ImB from the upper side and the left side of the second short axis image display area G2 in a rectangular shape is calculated and output.

According to the blood vessel ultrasonic image measuring method of this embodiment, since the pattern recognition for recognizing the image of the blood vessel 20 is executed with the Doppler signal included in the image of the blood vessel 20 in the ultrasound images in the first short axis image display area G1 and the second short axis image display area G2 from the first short axis ultrasonic array probe A and the second short axis ultrasonic array probe B, more accurate pattern recognition is enabled. Since the template patching technique is used for the pattern recognition, this embodiment is simplified and enables rapid arithmetic processes as compared to the case of using other pattern recognition techniques, for example, the NN (nearest neighbor) technique or the K-means technique.

Fourth Embodiment

Figure 28:
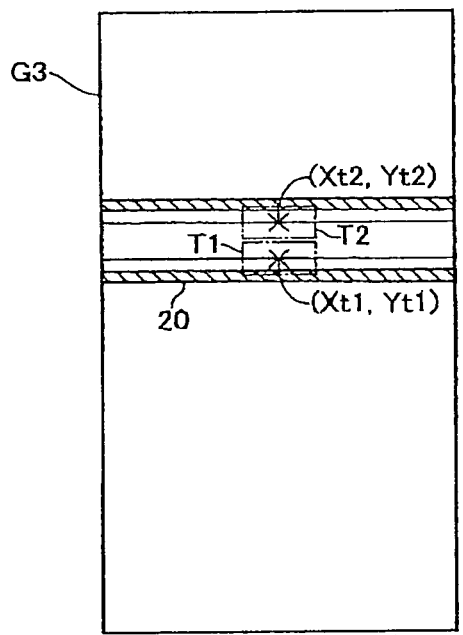
FIG. 28 is a diagram of a long axis image display area and a template used for a blood vessel diameter calculating step in another embodiment of the present invention.

FIG. 28 is a diagram for explaining the blood vessel diameter calculating step in another embodiment of the present invention. In this embodiment, as depicted in FIG. 28, the display control portion of the electronic control device 28 automatically recognizes points located on a line orthogonally intersecting with the longitudinal center line of the blood vessel 20 in the long axis image display area G3 and respectively coinciding with a template T1 centering on a point (Xt1, Yt1) located on the blood vessel lumen wall on the distal side, i.e., on the lower side of FIG. 28 and a template T2 centering on a point (Xt2, Yt2) located on the blood vessel lumen wall on the proximal side, i.e., on the upper side of FIG. 28, and the blood vessel wall in the long axis image of the blood vessel 20 to automatically calculate the lumen diameter as Yt1-Yt2.

Since the blood vessel ultrasonic image measuring method of this embodiment includes the blood vessel diameter calculating step of calculating the lumen diameter of the blood vessel 20 based on the long axis image signal of the blood vessel 20 detected by the long axis ultrasonic array probe C, the blood vessel diameter may accurately be acquired.

Fifth Embodiment

Figure 29:
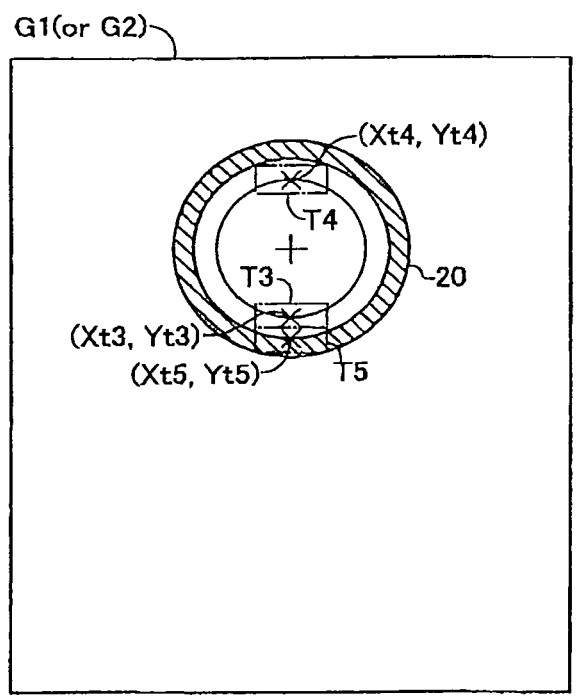
FIG. 29 is a diagram of a short axis image display area and a template used for a blood vessel parameter calculating step in another embodiment of the present invention.

FIG. 29 is a diagram for explaining the blood vessel parameter calculating step in another embodiment of the present invention. In this embodiment, as depicted in FIG. 29, the display control portion of the electronic control device 28 automatically recognizes points located on a line passing through the center of the blood vessel 20 in the first short axis image display area G1 or the second short axis image display area G2 and respectively coinciding with a template T3 centering on a point (Xt3, Yt3) located on the blood vessel lumen wall on the distal side, i.e., on the lower side of FIG. 29 and a template T4 centering on a point (Xt4, Yt4) located on the blood vessel lumen wall on the proximal side, i.e., on the upper side of FIG. 29, and the blood vessel wall in the short axis image of the blood vessel 20 to automatically calculate the lumen diameter as Yt3-Yt4. The display control portion of the electronic control device 28 then automatically recognizes a point located on a line passing through the center of the blood vessel 20 in the first short axis image display area G1 or the second short axis image display area G2 and coinciding with a template T5 centering on a point (Xt5, Yt5) located on the inner surface of the blood vessel outer wall on the distal side, i.e., on the lower side of FIG. 29 to automatically calculate the intima-media thickness as Yt5-Yt3.

Since the blood vessel ultrasonic image measuring method of this embodiment includes the blood vessel parameter calculating step of calculating the lumen diameter and the intima-media thickness of the blood vessel 20 based on the short axis image signal of the blood vessel 20 detected by the first short axis ultrasonic array probe A or the second short axis ultrasonic array probe B, the lumen diameter and the intima-media thickness may accurately be acquired.

Sixth Embodiment

FIG. 30 is a diagram of a positioning state display area G4 of the monitor screen displaying device in another embodiment of the present invention. In this embodiment, in the positioning state display area G4, a control step is executed to display in the positioning state display area G4 a symbol 104 that moves along the width direction, which is one of a first direction and a second direction orthogonal to each other, to indicate the distances c and d from the short axis image of the blood vessel 20 displayed in the first short axis image display area G1 to the edges on the both sides of the first short axis image display area G1, that moves along the longitudinal direction, which is the other of the first direction and the second direction orthogonal to each other, to indicate the distances e and f from the short axis image of the blood vessel 20 displayed in the second short axis image display area G2 to the edges on the both sides of the second short axis image display area G2, and that tilts to indicate a difference between the distance from the short axis image of the blood vessel 20 displayed in the first short axis image display area G1 to the upper edge or the lower edge of the first short axis image display area G1 and the distance from the short axis image of the blood vessel 20 displayed in the second short axis image display area G2 to the upper edge or the lower edge of the second short axis image display area G2.

The symbol 104 is consisting of a circle having a long line 106 and a short line 108 orthogonally intersecting at the center. As a result of the execution of the positioning process depicted in FIGS. 10 to 14, in the positioning state display area G4, a ratio between the distance from the center position of the symbol 104 to the left edge in the width direction of the positioning state display area G4 and the distance from the center position of the symbol 104 to the right edge in the width direction of the positioning state display area G4 is displayed to be equal to a ratio between the distance c and the distance d as a result of the control; a ratio between the distance to the upper edge in the longitudinal direction of the positioning state display area G4 and the distance from the center position of the symbol 104 to the edge in the longitudinal direction of the positioning state display area G4 is displayed to be equal to a ratio between the distance f and the distance e as a result of the control; and as the ultrasonic probe 24 comes closer to a predetermined position, i.e., a positioning completion position, the long line 106 of the symbol 104 is displayed with a smaller tilt in the width direction of the positioning state display area G4 and eventually with no tilt as a result of the control.

Figure 30A:
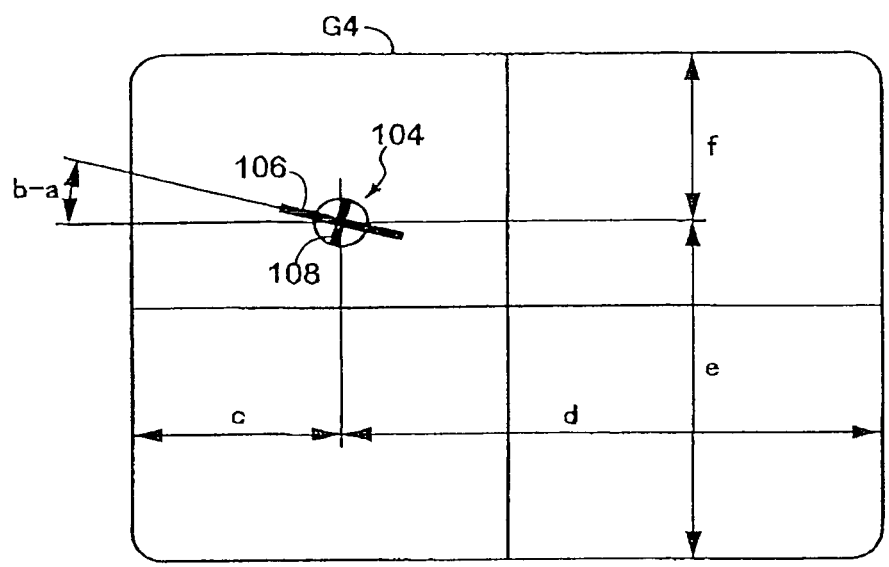
FIG. 30 is a diagram of a positioning state display area of the display screen of the monitor screen displaying device in another embodiment of the present invention.
Figure 30B:
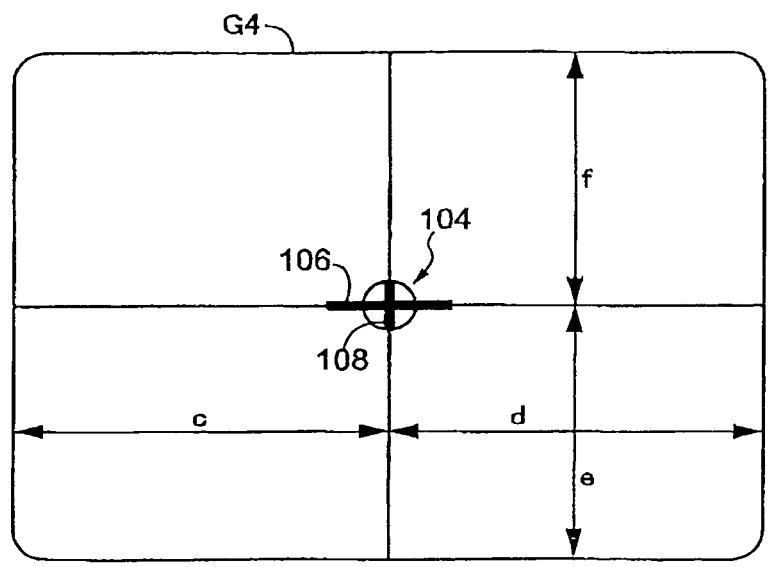

FIG. 30(a) depicts a state of the insufficient positioning control with a<b, c<d, and e>f. On the other hand, FIG. 30(b) is a diagram of the positioning state display area G4 in the normal state of the positioning control. The distance a from the first short axis ultrasonic array probe A to the center of the blood vessel 20 is equal to the distance b from the second short axis ultrasonic array probe B to the center of the blood vessel 20, and the image of the blood vessel 20 is positioned at the center portion in the width direction of the first short axis image display area G1, and the image of the blood vessel 20 is positioned at the center portion in the width direction of the second short axis image display area G2 in this state, which satisfies a=b, c=d, and e=f.

According to the blood vessel ultrasonic image measuring method of this embodiment, since the symbol 104 is displayed in the positioning state display area G4, that moves along the width direction, which is one of the first direction and the second direction orthogonal to each other, to indicate the distances c and d from the short axis image of the blood vessel 20 displayed in the first short axis image display area G1 to the edges on the both sides of the first short axis image display area G1, that moves along the longitudinal direction, which is the other of the first direction and the second direction orthogonal to each other, to indicate the distances e and f from the short axis image of the blood vessel 20 displayed in the second short axis image display area G2 to the edges on the both sides of the second short axis image display area G2, and that tilts to indicate a difference between the distance from the short axis image of the blood vessel 20 displayed in the first short axis image display area G1 to the upper edge or the lower edge of the first short axis image display area G1 and the distance from the short axis image of the blood vessel 20 displayed in the second short axis image display area G2 to the upper edge or the lower edge of the second short axis image display area G2 in the positioning state display area G4, the right and the wrong of the positioning of the ultrasonic probe 24 may visually and instantly be checked based on the position and the tilt of the symbol 104.

Seventh Embodiment

Figure 31:
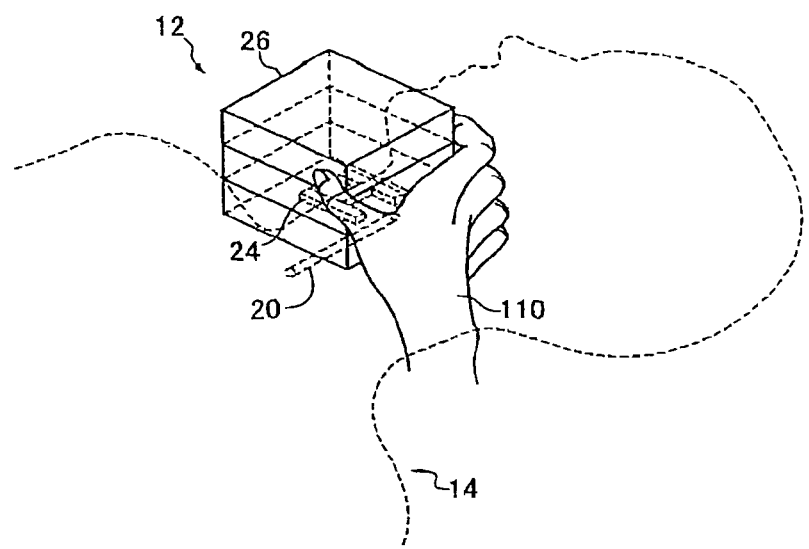
FIG. 31 is a diagram of a state of performing measurement with the hybrid probe unit held by hand in another embodiment of the present invention.
Figure 32:
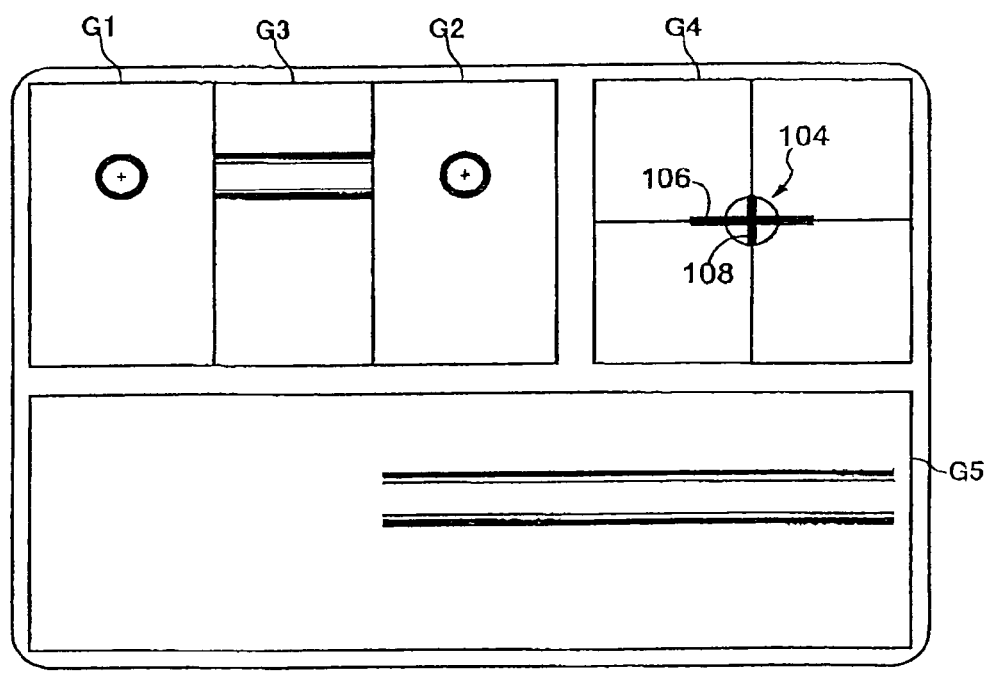
FIG. 32 is a diagram of an example of a display screen of the monitor screen displaying device in the embodiment depicted in FIG. 31.

FIG. 31 is a diagram of a holding configuration of the hybrid probe unit 12 in another embodiment of the present invention. The hybrid probe unit 12 of this embodiment is held by measurer's hand 110. FIG. 32 depicts an example of a display screen of the monitor screen displaying device 30 in this embodiment and the monitor screen displaying device 30 has a synthetic long axis image display area G5 for displaying an ultrasonic image longer than the display length of the long axis image display area G3.

Figure 33A:
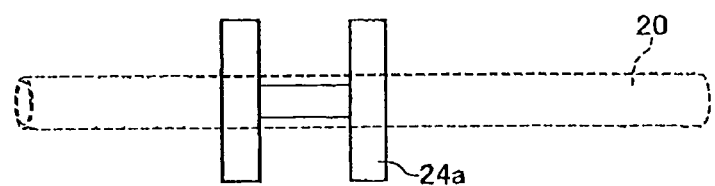
FIG. 33 is a diagram of the relative position between the ultrasonic probe and a blood vessel for each predetermined distance when the hybrid probe unit of FIG. 31 is moved along the blood vessel.

At the time of measurement, the electronic control device 28 executed the control operation as a real-time process to generate and display on the monitor screen displaying device 30 the short axis images and the long axis image of the blood vessel 20 located immediately under the ultrasonic probe 24 as described in the preceding embodiments. The process is executed at predetermined time interval, for example, at minimal time intervals of 20 msec. The operation of movement in the substantially longitudinal direction of the blood vessel 20 is performed by the hand 110 for the hybrid probe unit 12 having the ultrasonic probe 24. FIG. 33 is a diagram of the relative position between the ultrasonic probe 24 and the blood vessel 20 for each predetermined distance of the operation. FIG. 33(a) depicts an ultrasonic probe 24a at the measurement start position.

Figure 33B:
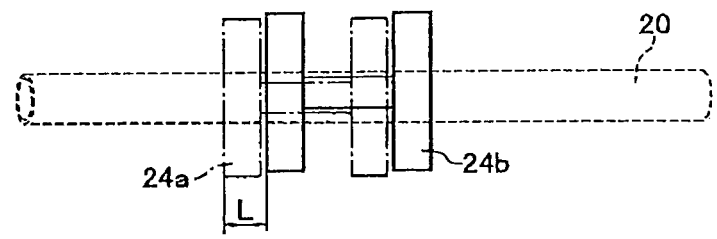
Figure 34:
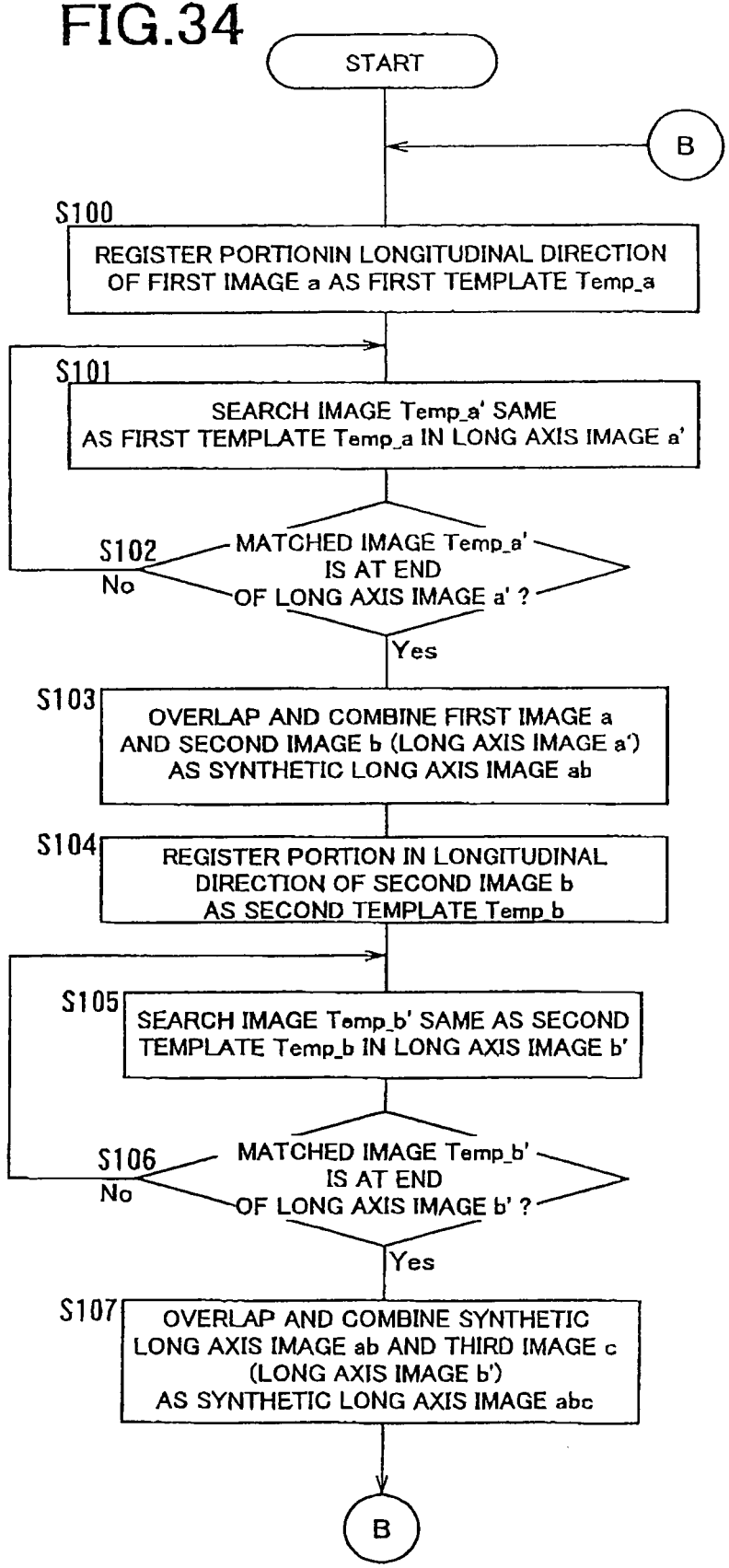
FIG. 34 is a flowchart for explaining a portion of the control operation of the electronic control device in the embodiment depicted in FIG. 31.
Figure 35:
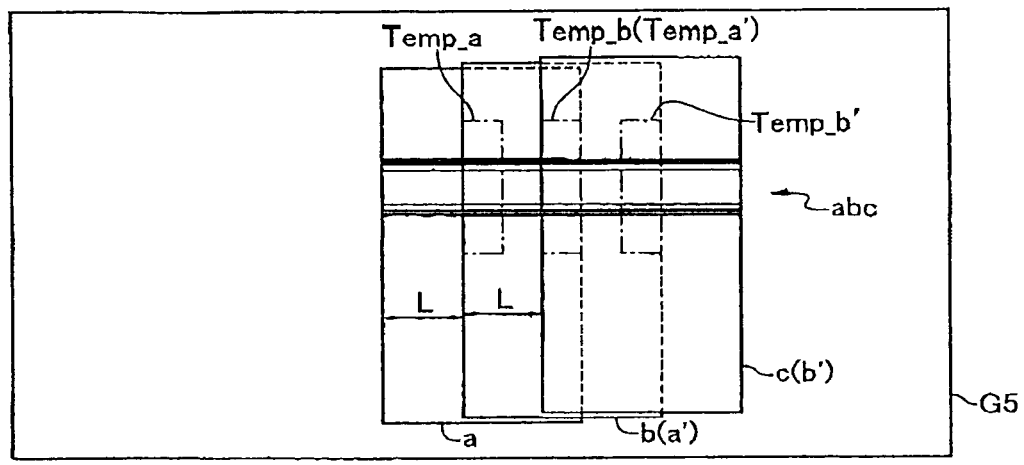
FIG. 35 is a diagram of a long axis synthetic image display area that displays a generated long axis synthetic image in the embodiment depicted in FIG. 31.

FIG. 34 is a flowchart, for explaining a relevant part of control operation of the electronic control device 28 for the operation and FIG. 35 is a diagram of the synthetic long axis image display area G5 of the monitor screen displaying device 30 that displays a synthetic long axis image abc generated as a result of the control operation. In FIGS. 34 and 35, first, at S100, an image of the blood vessel 20 displayed in the long axis image display area G3 generated at the measurement start position is stored as a first image a, and a portion in the longitudinal direction of the first image a is registered as a first template Temp_a. At S101, a long axis image a' generated after the minimal time interval from the measurement start position is searched, i.e., subjected to the pattern recognition using the template matching technique, for an image Temp_a', which is a portion in the longitudinal direction of the long axis image a' that is the same image as the first template Temp_a_a. At S102, it is determined whether the searched image Tempa_a' is positioned at the end of the long axis image display area G3 set in advance. The determination at S102 is positive when the ultrasonic probe 24a is moved in the longitudinal direction of the blood vessel 20 by a distance L from the left edge in the width direction of the first template Temp_a to the left edge in the width direction of the long axis image a or from the right edge in the width direction of the template Temp_a to the right edge in the width direction of the long axis image a, and this state is depicted in FIG. 33(b). While the determination at S102 is negative, S101 and S102 are repeatedly executed in sequence. If the determination at S102 is positive, the long axis image a' is registered as a second image b and, at S103, the first image a and the second image b are combined such that the first template Temp_a and the image Temp_a' included in the respective images are overlapped with each other for registration as a synthetic long axis image ab, which is displayed in the synthetic long axis image display area G5.

Figure 33C:
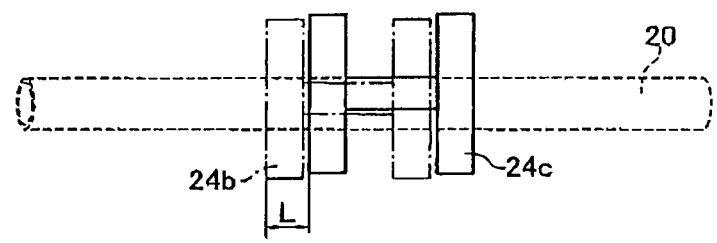

Subsequently, at S104, a portion in the longitudinal direction of the second image b is registered as a second template Temp_b. At S105, a long axis image b' generated after the minimal time interval is searched, i.e., subjected to the pattern recognition using the template matching technique, for an image Temp_b', which is a portion in the longitudinal direction of the long axis image a' that is the same image as the second template Temp_b. At S106, it is determined whether the searched image Temp_b' is positioned at the end of the long axis image display area G3 set in advance. The determination at S106 is positive when an ultrasonic probe 24b is moved in the longitudinal direction of the blood vessel 20 by a distance L, and this state is depicted in FIG. 33(c). While the determination at S106 is negative, S105 and S106 are repeatedly executed in sequence. If the determination at S106 is positive, the long axis image b' is registered as a third image c and, at S107, the synthetic long axis image ab and the third image c are combined such that the second template Temp_b and the image Temp_b' included in the respective images are overlapped with each other for registration as the synthetic long axis image abc, which is displayed in the synthetic long axis image display area G5. Subsequently, S100 to S107 are repeatedly executed.

S100 corresponds to a step of storing an image of the blood vessel 20 displayed in the long axis image display area G3 as the first image a and registering a portion in the longitudinal direction of the image of the blood vessel 20 as the first template Temp_a in advance. S101, S102, and S104 correspond to a step of storing the long axis image a' of the blood vessel 20 displayed in the long axis image display area G3 as the second image b when the image Temp_a' of a portion in the longitudinal direction of the long axis image a' of the blood vessel 20 identical to the first template Temp_a arrives at the end of the long axis image display area G3 set in advance in the course of the movement of the ultrasonic probe 24 along the blood vessel 20 and registering the portion in the longitudinal direction of the long axis image a' of the blood vessel 20 as the second template Temp_b. S105 and S106 correspond to a step of storing the long axis image b' of the blood vessel 20 displayed in the long axis image display area G3 as the third image c when the image Temp_b' of a portion in the longitudinal direction of the long axis image b' of the blood vessel 20 identical to the second template Temp_b arrives at the end of the long axis image display area G3 set in advance in the course of the further movement of the ultrasonic probe 24 along the blood vessel 20. S103 and S107 correspond to a step of synthesizing and displaying in the synthetic long axis image display area G5 one long axis image, i.e., the synthetic long axis image, longer than the longitudinal dimension of the image of the blood vessel 20 displayed in the long axis image display area G3 from the first image a, the second image b, and the third image c.

Since the blood vessel ultrasonic image measuring method of this embodiment includes the step of storing the image of the blood vessel 20 displayed in the long axis image display area G3 as the first image a and registering a portion in the longitudinal direction of the image of the blood vessel 20 as the first template Temp_a in advance; the step of storing the long axis image a' of the blood vessel 20 displayed in the long axis image display area G3 as the second image b when the image Temp_a' of a portion in the longitudinal direction of the long axis image a' of the blood vessel 20 identical to the first template Temp_a arrives at the end of the long axis image display area G3 set in advance in the course of the movement of the ultrasonic probe 24 along the blood vessel 20 and registering the portion in the longitudinal direction of the long axis image a' of the blood vessel 20 as the second template Temp_b; the step of storing the long axis image b' of the blood vessel 20 displayed in the long axis image display area G3 as the third image c when the image Temp_b' of a portion in the longitudinal direction of the long axis image b' of the blood vessel 20 identical to the second template Temp_b arrives at the end of the long axis image display area G3 set in advance in the course of the further movement of the ultrasonic probe 24 along the blood vessel 20; and the step of synthesizing and displaying in the synthetic long axis image display area G5 one long axis image longer than the longitudinal dimension of the image of the blood vessel 20 displayed in the long axis image display area G3 from the first image a, the second image b, and the third image c, the long axis image of the blood vessel 20 longer than the length of the long axis ultrasonic array probe C may be acquired. Since the template patching technique is used for the pattern recognition, this embodiment is simplified and enables rapid arithmetic processes as compared to the case of using other pattern recognition techniques, for example, the NN (nearest neighbor) technique or the K-means technique.

According to the blood vessel ultrasonic image measuring method of this embodiment, the measurement may be made in such a case that the setup with the sensor holder 10 is difficult or that no suitable platform exists to measure an unscheduled site. For example, this corresponds to the case of measuring a carotid artery, etc. Although the same applies to the embodiments, even if the positional relationship between the blood vessel 20 and the probe 24 is changed during the measurement in such a handheld measurement, the probe 24 is quickly returned to a predetermined position through the automatic control by the electronic control device 28, i.e., the automatic tracking of the blood vessel 20 is enabled and, therefore, the measurement may be made without requiring a skill of manual operation of an operator.

Eighth Embodiment

Figure 36:
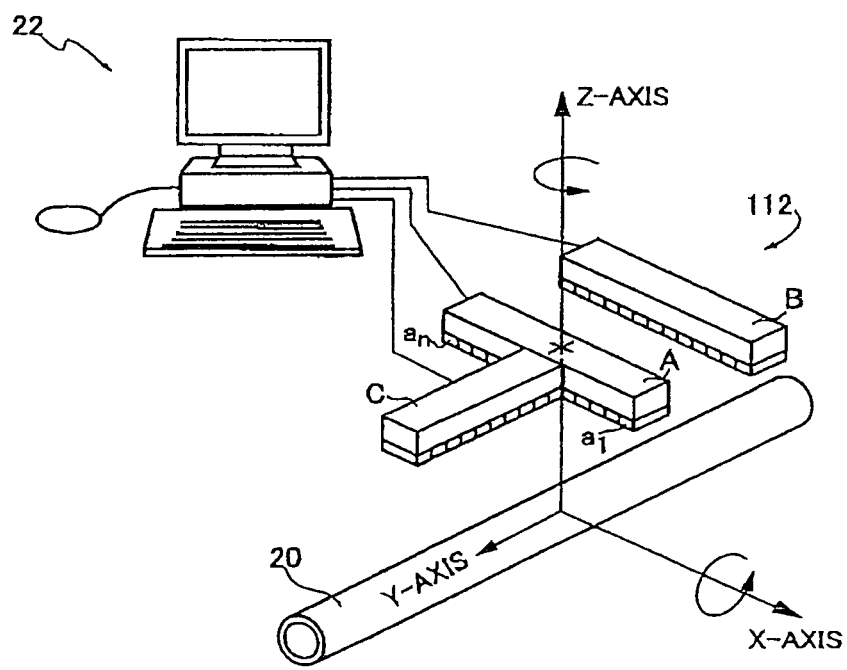
FIG. 36 is a diagram for explaining the ultrasonic probe and the XYZ-axis orthogonal coordinate axes for representing a posture of the ultrasonic probe relative to a blood vessel, corresponding to FIG. 2.

FIG. 36 is a diagram for explaining an ultrasonic probe 112 and the XYZ-axis orthogonal coordinate axes for representing a posture of the ultrasonic probe 112 relative to the blood vessel 20. The ultrasonic probe 112 of this embodiment is made up of two lines of the first short axis ultrasonic array probe A and the second short axis ultrasonic array probe B parallel to each other and the long axis ultrasonic array probe C having the longitudinal direction orthogonal to the longitudinal direction of the first short axis ultrasonic array probe A and abutting on the longitudinal center portion of the first short axis ultrasonic array probe A on the side farther from the second short axis ultrasonic array probe B on one flat surface, i.e., the flat probing surface 27.

The X-axis is defined as a direction that is parallel to the longitudinal direction of the first short axis ultrasonic array probe A, that is located immediately under the first short axis ultrasonic array probe A, and that passes through or in the vicinity of the blood vessel 20; the Y-axis is defined as a direction that is parallel to the longitudinal direction of the long axis ultrasonic array probe C and that is orthogonal to the X-axis; and the Z-axis is defined as a direction that passes through the intersecting point between the longitudinal direction of the first short axis ultrasonic array probe A and the longitudinal direction of the long axis ultrasonic array probe C and that is orthogonal to the X-axis direction and the Y-axis direction. The ultrasonic probe 112 is translated in the X-axis direction and rotated around the X-axis and the Z-axis by the multiaxis driving device 26.

Although the ultrasonic probe 112 of this embodiment is different in the position of the long axis ultrasonic array probe C relative to the first short axis ultrasonic array probe A and the second short axis ultrasonic array probe B as compared to the ultrasonic probe 24 of the first embodiment, the longitudinal direction thereof has the positional relationship orthogonal to the longitudinal direction of the first short axis ultrasonic array probe A and exits on one flat surface, i.e., the flat probing surface 27 along with the first short axis ultrasonic array probe A and the second short axis ultrasonic array probe B in the same way. Therefore, the positioning of the ultrasonic probe 112 depicted in FIG. 36 to a predetermined position may be achieved with the same method as the positioning of the ultrasonic probe 24 depicted in FIG. 24 to the predetermined position. Therefore, according to the blood vessel ultrasonic image measuring method of this embodiment, the effect acquired in the first embodiment may be enjoyed in the same way.

Although the embodiments of present invention have been described in detail with reference to the drawings, the present invention is not limited to these embodiments and may be implemented in other aspects.

For example, although the embodiments include the long axis ultrasonic array probe C and the long axis image display area G3 that displays the ultrasonic image from the long axis ultrasonic array probe C, these are not necessarily essential. Although the long axis image display area G3 is disposed adjacently to the first short axis image display area G1 and the second short axis image display area G2, the long axis image display area G3 may be disposed adjacently to the first short axis image display area G1 on the side farther from the second short axis image display area G2 or, conversely, the long axis image display area G3 may be disposed adjacently to the second short axis image display area G2 on the side farther from the first short axis image display area G1 in the eighth embodiment, for example.

Although the X-axis is defined as a direction that is parallel to the longitudinal direction of the first short axis ultrasonic array probe A, that is located immediately under the first short axis ultrasonic array probe A, and that passes through the blood vessel 20 in the embodiment, the X-axis may not necessarily pass through the blood vessel 20. The X-axis may be coaxial with the longitudinal direction of the first short axis ultrasonic array probe A.

In the embodiments, the long axis ultrasonic array probe C links the longitudinal center potions of the first short axis ultrasonic array probe A and the second short axis ultrasonic array probe B or is located with the longitudinal direction orthogonal to the longitudinal direction of the first short axis ultrasonic array probe A at the longitudinal center portion of the first short axis ultrasonic array probe A on the side farther from the second short axis ultrasonic array probe B. However, the long axis ultrasonic array probe C may not necessarily be located at the center of the first short axis ultrasonic array probe A. The long axis ultrasonic array probe C may not necessarily abut on the first short axis ultrasonic array probe A or may be located and abut on the longitudinal center portion of the second short axis ultrasonic array probe B on the side farther from the first short axis ultrasonic array probe A.

The mechanical configurations of the X-axis rotating mechanism 56, the X-axis translating mechanism 58, and the Z-axis rotating mechanism 60 are disclosed as an example in the embodiments and may be implemented with other mechanical configurations.

Although the sensor holder 10 is fixed to a desk, a pedestal, etc., by the magnetic block 36 that is a constituent element thereof in the embodiments, the fixation may be achieved by suction force by the negative pressure generated or supplied on the contact surface, the fastening force of a fixing tool passing through a long hole penetrating the pedestal, etc., instead of utilizing the magnetic attracting force of permanent magnet or electric magnet as above.

Although the sensor holder 10 made up of the two links 46, 47 or the hand held operation is used for holding the hybrid probe unit 12 in the embodiments, a sensor holder with another configuration including a telescopic arm, a robot arm, etc., may be used.

Although the first short axis ultrasonic array probe A and the second short axis ultrasonic array probe B emits ultrasonic obliquely at the predetermined angle α and angle β in directions toward the upstream of the blood vessel 20 to the blood vessel 20 in the blood flowing state in the direction of the arrow I of FIG. 25(a) in the second embodiment, the probes may emit ultrasonic obliquely at the predetermined angle α and angle β in directions toward the downstream of the blood vessel 20.

Only some embodiments have been described and, although not exemplary illustrated one by one, the present invention may be implemented in variously modified or altered aspects based on the knowledge of those skilled in the art without departing from the spirit thereof.

The invention claimed is:

1. A blood vessel ultrasonic image measuring method, the method comprising:
arranging a first short axis ultrasonic array probe and a second short axis ultrasonic array probe of an ultrasonic probe such that the first short axis ultrasonic array probe and the second short axis ultrasonic array probe are parallel to each other and arranging a long axis ultrasonic array probe of the ultrasonic probe such that the long axis ultrasonic array probe abuts the first short axis ultrasonic array probe and/or the second short axis ultrasonic array probe, on one flat surface, the first short axis ultrasonic array probe and the second short axis ultrasonic array probe having a plurality of ultrasonic transducers linearly arranged along a direction parallel to an X-axis direction, and the long axis ultrasonic array probe having a plurality of ultrasonic transducers linearly arranged in a Y-axis direction orthogonal to the X-axis direction, rotating the ultrasonic probe around the X-axis with a positioning device, moving the ultrasonic probe in the X-axis direction with the positioning device, and rotating the ultrasonic probe around a Z-axis with the positioning device, the Z-axis passing directly through a longitudinal center portion of the first short axis ultrasonic array probe, passing directly through an intersecting point between a longitudinal direction of the first short axis ultrasonic array probe and a longitudinal direction of the long axis ultrasonic array probe being orthogonal to the X-axis direction and the Y-axis direction, and being orthogonal to the one flat surface, and displaying an ultrasonic image from the first short axis ultrasonic array probe with an image displaying device including a first short axis image display area, displays an ultrasonic image from the second short axis ultrasonic array probe with a second short axis image display area, and displaying an ultrasonic image from the long axis ultrasonic array probe with a long axis image display area to bring the ultrasonic probe into contact with skin of a living body for measuring an ultrasonic image of a blood vessel under the skin of the living body;

an around-X-axis positioning step of causing the positioning device to position the ultrasonic probe around the X-axis such that a distance from the first short axis ultrasonic array probe to a center of the blood vessel becomes equal to a distance from the second short axis ultrasonic array probe to the center of the blood vessel;

an X-axis direction positioning step of causing the positioning device to translate the ultrasonic probe in the X-axis direction such that the ultrasonic image of the blood vessel is positioned at a center portion in a width direction of the first short axis image display area, subsequent to the around X-axis positioning step;

an around Z-axis positioning step of causing the positioning device to rotate the ultrasonic probe around the Z-axis such that a cross-sectional image of the blood vessel is positioned at a center portion in a width direction of the second short axis image display area and a longitudinal-section image of the blood vessel is positioned parallel to a width direction of the long axis image display area, subsequent to the X-axis direction positioning step; and calculating lumen diameter, intima thickness and/or intima-media thickness of the blood vessel based on a distance between intersecting points between a line profile indicative of a luminance in a transverse direction of the blood vessel in the long axis image display area displaying the ultrasonic image from the long axis ultrasonic array probe and a predetermined luminance determination line, subsequent to the around Z-axis positioning step;

wherein at the around-X-axis positioning step, the X-axis direction positioning step, or the around Z-axis positioning step, a pattern recognition is executed for recognizing the ultrasonic image of the blood vessel.

2. The blood vessel ultrasonic image measuring method of claim 1, wherein the image displaying device includes the long axis image display area that abuts on the first short axis image display area and/or the second short axis image display area, and wherein the first short axis image display area, the second short axis image display area, and the long axis image display area has a common longitudinal axis indicative of a depth dimension from the skin.

3. The blood vessel ultrasonic image measuring method of claim 1, further comprising emitting ultrasonic emissions obliquely at predetermined angles relative to the blood vessel in directions upstream or downstream of the blood vessel with the first short axis ultrasonic array probe and the second short axis ultrasonic array probe.

4. The blood vessel ultrasonic image measuring method of claim 3, further comprising correcting short axis ultrasonic images respectively displayed in the first short axis image display area and the second short axis image display area based on the predetermined angles to form images in a state that the ultrasonic emission direction of the first short axis ultrasonic array probe and the second short axis ultrasonic array probe is orthogonal to the blood vessel when short axis ultrasonic images of the blood vessel respectively detected by the first short axis ultrasonic array probe and the second short axis ultrasonic array probe are respectively displayed in the first short axis image display area and the second short axis image display area.

5. The blood vessel ultrasonic image method of claim 1, further comprising executing the pattern recognition with a Doppler signal included in the ultrasonic image of the blood vessel in the ultrasonic images in the first short axis image display area and the second short axis image display area from the first short axis ultrasonic array probe and the second short axis ultrasonic array probe.

6. The blood vessel ultrasonic image measuring method of claim 1, further comprising calculating the lumen diameter and/or the intima-media thickness of the blood vessel based on the ultrasonic image from the first short axis array probe or the second short axis ultrasonic array probe.

7. The blood vessel ultrasonic image measuring method of claim 2, further comprising displaying a symbol in a positioning state display area, the symbol in the positioning state display area moving along one of a first direction and a second direction orthogonal to each other to indicate distances from the ultrasonic image from the first short axis ultrasonic array probe displayed in the first short axis image display area to edges on both sides of the first short axis image display area, the symbol moving along the other of the first direction and the second direction orthogonal to each other to indicate distances from the ultrasonic image from the second short axis ultrasonic array probe displayed in the second short axis image display area to edges on both sides of the second short axis image display area, the symbol tilting to indicate a difference between a distance from the ultrasonic image from the first short axis ultrasonic array probe displayed in the first short axis image display area to the upper edge or the lower edge of the first short axis image display area and a distance from the ultrasonic image from the second short axis ultrasonic array probe displayed in the second short axis image display area to the upper edge or the lower edge of the second short axis image display area.

8. The blood vessel ultrasonic image measuring method of claim 2, further comprising:

storing the ultrasonic image of the blood vessel displayed in the long axis image display area as a first image and registering a portion in a longitudinal direction of the ultrasonic image of the blood vessel as a first template in advance, storing the ultrasonic image of the blood vessel displayed in the long axis image display area as a second image when a portion in the longitudinal direction of the ultrasonic image of the blood vessel identical to the first template arrives at an end of the long axis image display area set in advance in the course of movement of the ultrasonic probe along the blood vessel and registering the portion in the longitudinal direction of the ultrasonic image of the blood vessel as a second template, storing the ultrasonic image of the blood vessel displayed in the long axis image display area as a third image when a portion in the longitudinal direction of the ultrasonic image of the blood vessel identical to the second template arrives at an end of the long axis image display area set in advance in the course of further movement of the ultrasonic probe along the blood vessel, and synthesizing and displaying in a synthetic long axis image display area one long axis image longer than a longitudinal dimension of the ultrasonic image of the blood vessel from the first image, the second image, and the third image.

9. The blood vessel ultrasonic image measuring method as recited in claim 1, the X-axis direction positioning step further comprising:

determining a first distance between a first end of the first short axis image display area and a first intersection point where the longitudinal center of the blood vessel intersects with first short axis image display area, determining a second distance between a second end of the first short axis image display area and the first intersection point, determining whether the first distance and the second distance are equal, and further moving the ultrasonic probe in the X-axis direction if the first distance and the second distance are not equal.

10. The blood vessel ultrasonic image measuring method as recited in claim 1, the around-Z-axis positioning step further comprising:

determining a third distance between a first end of the second short axis image display area and a second intersection point where the longitudinal center of the blood vessel intersects with second short axis image display area, determining a fourth distance between a second end of the second short axis image display area and the second intersection point, determining whether the third distance and the fourth distance are equal, further rotating the ultrasonic probe relative to the Z-axis if the third distance and the fourth distance are not equal.

* * * * *